US006287787B1

(12) United States Patent
Houghten et al.

(10) Patent No.: US 6,287,787 B1
(45) Date of Patent: Sep. 11, 2001

(54) DIMERIC OLIGOPEPTIDE MIXTURE SETS

(75) Inventors: Richard A. Houghten, Solana Beach; Clemencia Pinilla, Cardiff, both of CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 0 days.

(21) Appl. No.: 08/157,562

(22) Filed: Nov. 24, 1993

(51) Int. Cl.$^7$ .................................................. G01N 33/567
(52) U.S. Cl. .................. 435/7.21; 435/7.1; 436/501; 436/518; 530/300; 530/327; 530/328; 530/329; 530/330; 530/333; 530/334; 530/335; 530/336; 530/345
(58) Field of Search ....................... 435/7.1, 7.21; 436/501, 518; 530/300, 327, 328, 329, 330, 333, 334, 335, 336, 345

(56) References Cited

U.S. PATENT DOCUMENTS

| | | | |
|---|---|---|---|
| 4,631,211 | 12/1986 | Houghten | 428/35 |
| 4,708,871 | 11/1987 | Geysen | 424/88 |
| 4,833,092 | 5/1989 | Geysen | 436/501 |
| 5,010,175 | 4/1991 | Rutter et al. | 530/334 |
| 5,182,366 | 1/1993 | Huebner | 530/334 |
| 5,194,392 | 3/1993 | Geysen | 436/518 |
| 5,202,418 | 4/1993 | Lebl et al. | 530/334 |

FOREIGN PATENT DOCUMENTS

| | | |
|---|---|---|
| WO 84/03506 | 9/1984 | (WO) . |
| WO 84/03564 | 9/1984 | (WO) . |
| 8901943 * | 3/1989 | (WO) . |
| WO 92/0091 | 1/1992 | (WO) . |
| WO 92/09300 | 6/1992 | (WO) . |

OTHER PUBLICATIONS

Journal of Medicinal Chemistry, 1990 vol. 33 No. 9 pp. 2552–2559.
Authors: Anand S. Dutta, James J. Gormley, Peter F. McLaughlin, and John S. Major.
Merrifield et al. *J. Amer. Chem. Soc.*, 85:2149–2154 (1963).
Houghten, *Proc. Natl. Acad. Sci.*, 82:5131–5135 (1985).
Houghten et al., *Int. J. Peptide Protein Res.*, 27:673–678 (1986).
Houghten et al., *Biotechniques*, 4(6):522–528 (1986).
Geysen et al., *Proc. Natl. Acad. Sci. U.S.A.*, 81:3998–4002 (1984).
Geysen et al., *Proc. Natl. Acad. Sci. U.S.A.*, 82:178–182 (1985).
Geysen et al., in *Synthetic Peptides as Antigens*, 130–149 (1986).
Geysen et al., *J. Immunol. Meth.*, 102:259–274 (1987).
Schoofs et al., *J. Immunol.*, 140:611–616 (1988).
Furka et al., 1988, 14th International Congress of Biochemistry, vol. 5, Abstract FR:013.

1988, Xth International Symposium on Medicinal Chemistry, Budapest, Abstract 288, p. 168.
Furka et al., *Int. J. Peptide Protein Res.*, 37:487–493 (1991).
Lam et al., *Nature*, 354:82–84 1991).
Devlin et al., *Science*, 249:404–405 (1990).
Scott et al., *Science*, 249:386–390 (1990).
Fodor et al., *Science*, 251:767–773 (1991).
Houghten et al., *Nature*, 354:84–86 (1991).
Pinilla et al., *Vaccines 92*, Cold Spring Harbor Laboratory Press, Cold Spring Harbor, pp. 25–27 (1992).
Appel et al., *Immunomethods*, 1:17–23 (1992).
Houghten et al., *BioTechniques*, 13:412–421 (1992).
Houghten et al., in *Innovation and Perspectives in Solid Phase Syntheses: Peptides, Polypeptides and Oligonucleotides*, R. Epton (ed.), Intercept, Ltd., Andover, pp. 237–239 (1992).
Houghten et al., in *Peptides*, J.A. Smith and J.E. Rivier (eds.), Proceedings of the Twelfth American Peptide Symposium, ESCOM, Leiden, pp. 560–561 (1992).
Pinilla et al., *BioTechniques*, 13:901–905 (1992).
Horton et al., *Proceedings of the 13th American Peptide Symposium*, R. Hodges, ed. ESCOM, (1994), in press, Abstract LF3 (Jun. 1993).
Chan, *Biochemistry*, 7:4247–4254 (1968).
Wilson et al., *Cell*, 37:767–778 (1984).
Sheriff et al., *Proc. Natl. Acad. Sci., USA*, 84:8075–8079 (1987).
Pasternak et al., *Mol. Pharm.*, 11:340–351 (1975).
Bradford, *Anal. Biochem.*, 72:248–254 (1976).
Simon et al., *Proc. Natl. Acad. Sci., USA*, 89:9367–9371 (1992).
J. Coombs, *Dictionary of Biotechnology*, 2nd ed., Stockton Press, New York (1992), pp. 280, 287, 308 and 335.
A. White et al., *Principles of Biochemistry*, 6th ed., McGraw–Hill Book Co., New York (1978), p. 132.

* cited by examiner

*Primary Examiner*—Jyothsna Venkat
(74) *Attorney, Agent, or Firm*—Welsh & Katz, Ltd.

(57) ABSTRACT

Dimeric oligopeptide mixture sets, their synthesis and use in determining the sequence of an oligopeptide dimer ligand that optimally binds to a receptor are disclosed. A dimeric oligopeptide mixture set has two oligopeptide portions bonded together by a disulfide bond. Each oligopeptide of a first oligopeptide portion has the same number of 3 to about 10 residues including an oxidized mercaptan-containing residue that forms part of the disulfide bond and an amino acid residue sequence that includes at least one of at least six residues in addition to the oxidized mercaptan-containing residue at the same one or more predetermined positions of the oligopeptide chain. The second portion has an oligopeptide chain having a length of 4 to about 10 residues, including an oxidized mercaptan-containing residue that forms part of the disulfide bond. The second portion is a mixture whose chains have equimolar amounts of those at least six amino acid residues at the same one or more other positions of the oligopeptide chain.

29 Claims, No Drawings

DIMERIC OLIGOPEPTIDE MIXTURE SETS

DESCRIPTION

1. Technical Field

The present invention relates to the synthesis and use of peptide-like mixtures. More particularly, the invention relates to the synthesis and use of a mixture of dimer oligopeptide sets.

2. Background and Related Art

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.*, 85:2149–2154 (1963). The "Merrifield method" has for the most part remained largely unchanged and is used in nearly all automated peptide synthesizers available today.

In brief, the Merrifield method involves synthesis of a peptide chain on solid support resin particles. These particles typically are comprised of polystyrene cross-linked with divinyl benzene to form porous beads that are insoluble in both water and various organic solvents used in the synthesis protocol. The resin particles contain a fixed amount of amino- or hydroxylmethyl aromatic moiety that serves as the linkage point for the first amino acid in the peptide.

Attachment of the first amino acid entails chemically reacting its carboxyl-terminal (C-terminal) end with derivatized resin to form the carboxyl-terminal end of the oligopeptide. The alpha-amino end of the amino acid is typically blocked with a t-butoxy-carbonyl group (t-BOC) or with a 9-fluorenylmethyloxycarbonyl (Fmoc) group to prevent the amino group that could otherwise react from participating in the coupling reaction. The side chain groups of the amino acids, if reactive, are also blocked (or protected) by various benzyl-derived protecting groups in the form of ethers, thioethers, esters, and carbamates, and t-butyl-derived blockers for Fmoc syntheses.

The next step and subsequent repetitive cycles involve deblocking the amino-terminal (N-terminal) resin-bound amino acid residue (or terminal residue of the peptide chain) to remove the alpha-amino blocking group, followed by chemical addition (coupling) of the next blocked amino acid. This process is repeated for however many cycles are necessary to synthesize the entire peptide chain of interest. After each of the coupling and deblocking steps, the resin-bound peptide is thoroughly washed to remove any residual reactants before proceeding to the next. The solid support particles facilitate removal of reagents at any given step as the resin and resin-bound peptide can be readily filtered and washed while being held in a column or device with porous openings such as a filter.

Synthesized peptides are released from the resin by acid catalysis (typically with hydrofluoric acid or trifluoroacetic acid), which cleaves the peptide from the resin leaving an amide or carboxyl group on its C-terminal amino acid. Acidolytic cleavage also serves to remove the protecting groups from the side chains of the amino acids in the synthesized peptide. Finished peptides can then be purified by any one of a variety of chromatography methods.

Though most peptides are synthesized with the above described procedure using automated instruments, a recent advance in the solid phase method by R. A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, Proc. Natl. Acad. Sci., 82:5131–5135 (1985); Houghten et al., Int. *J. Peptide Protein Res.*, 27:673–678 (1986); Houghten et al., *Biotechniques*, 4, 6, 522–528 (1986), and Houghten, U.S. Pat. No. 4,631,211, whose disclosures are incorporated by reference.

Illustratively, the SMPS process employs porous containers such as plastic mesh bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

The interest in obtaining biologically active peptides for pharmaceutical, diagnostic and other uses would make desirable a procedure designed to find a mixture of peptides or a single peptide within a mixture with optimal activity for a target application. screening mixtures of peptides enables the researcher to greatly simplify the search for useful therapeutic or diagnostic peptide compounds. Mixtures containing hundreds of thousands or more peptides are readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds because most are commonly present, and active, at nanomolar and lower concentrations. These compounds are also, in most instances, produced distant from their affection sites.

That a small peptide (or other molecule) can readily "find" an acceptor system, bind to it, and affect a necessary biological function prior to being cleared from the circulation or degraded suggests that a single specific peptide sequence can be present in a very wide diversity, and concentration, of other individual peptides and still be recognized by its particular acceptor system (antibody, cellular receptor, etc.). If one could devise a means to prepare and screen a synthetic library of peptides, then the normal exquisite selectivity of biological affector/acceptor systems could be used to screen through vast numbers of synthetic oligopeptides.

Of interest in screening very large numbers of peptides is work by Geysen et al., which deals with methods for synthesizing peptides with specific sequences of amino acids and then using those peptides to identify reactions with various receptors. See U.S. Pat. Nos. 4,708,871, 4,833,092 and 5,194,392; P.C.T. Publications Nos. WO 84/03506 and WO 84/03564; Geysen et al., *Proc. Natl. Acad. Sci. U.S.A.,* 81:3998–4002 (1984); Geysen et al., *Proc. Natl. Acad. Sci. U.S.A.,* 82:178–182 (1985); Geysen et al., in *Synthetic Peptides as Antigens,* 130–149 (1986); Geysen et al., *J. Immunol. Meth.,* 102:259–274 (1987); and Schoofs et al., *J. Immunol.,* 140:611–616 (1988).

In U.S. Pat. No. 5,194,392, Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule.

The mimotopes were synthesized on a series of solid polymer (e.g. polyethylene with a coating of grafted polyacrylic acid) rods having a diameter of about 4 mm and a length of about 50 mm. A spacer formed by reaction of the υ-amino group of t-BOC-lysine methyl ester and then t-BOC-alanine was added to the grafted polyacrylic acid resins, followed by removal of the t-BOC group to provide an amino group to be used to begin the syntheses.

A mixture of blocked (N-protected) amino acids containing different amounts of each of the blocked (N-protected) twenty amino acids to be used was dissolved in dimethyl formamide and then coupled to the rods. That first coupling was repeated three times using conventional solid phase synthesis techniques. Twenty amino acid residues were individually next added to different rods so that twenty rod-linked 5-mer peptide mixture sequences were prepared. Each sequence had a single, known amino acid residue at the amino-terminus and an alleged equimolar mixture of amino acid residues at each of the four other positions of the chain. Each of those twenty rod-linked peptides was then individually reacted with each of the twenty amino acid residues to form 400 (20×20) rod-linked 6-mer peptides having the two amino-terminal positions defined and the four remaining positions as mixtures. Two more positions of alleged equimolar mixtures of amino acids were then added, and the terminal amine acetylated to form N-acetyl 8-mers linked to the rods whose first two amino acid positions were undefined (mixtures), followed by two defined positions, followed by four undefined positions (mixtures), followed by the spacer and then the supporting rods.

The 400 rod-linked N-acetyl 8-mer peptide mixture preparations were then screened in an ELISA assay using a monoclonal antibody to a desired antigenic protein. The 8-mers having the preferential binding to the antibody were identified. Two sets of further 8-mers that contained the identified best-binding 2-mer sequences within those 8-mers were prepared.

A first set contained mixed amino acids at the three C-terminal positions, followed toward the N-terminus, by a position containing each of the twenty amino acids made by twenty separate couplings, the identified 2-mer sequences, two further mixtures at the next two positions, and an N-terminal acetyl group. The second group contained mixed amino acids at the four C-terminal positions, the identified 2-mer sequences, a position made by separate couplings of each of the twenty amino acids, mixed amino acids as the terminal residues and an N-terminal acetyl group.

Each of those rod-linked N-acetyl 8-mers was again screened in an ELISA with the monoclonal antibody. The preferential binding sequences for each group were identified, and thus 4-mer, preferential-binding sequences were identified.

The above process of separately adding each of the amino acids on either side of identified preferential-binding sequences was repeated until an optimum binding sequence was identified.

The above method, although elegant, suffers from several disadvantages as to peptides. First, owing to the small size of each rod used, relatively small amounts of each peptide is produced. Second, each assay is carried out using the rod-linked peptides, rather than the free peptides in solution so the method is not applicable to in vivo assays. Third, even though specific amounts of each blocked amino acid are used to prepare the mixed amino acid residues at the desired positions, there is no way of ascertaining that an equimolar amount of each residue is truly present at those positions. In addition, this patent teaches no way to remove the synthesized peptide mixtures from the rods.

U.S. Pat. No. 5,194,392 contains a table of specific amounts of each N-protected amino acid to use to provide alleged equimolarity. The prosecution history of that patent provides a revised table with different amounts of N-protected amino acids for use.

Rutter et al. U.S. Pat. No. 5,010,175 discloses the preparation of peptide mixtures that are said to contain equimolar amounts of each reacted amino acid at predetermined positions of the peptide chain. Those mixtures are also said to contain each peptide in retrievable and analyzable amounts and are constructed by reacting mixtures of activated amino acids in solution concentrations based on the relative coupling constants of those activated amino acids.

The mixture of amino acids used for syntheses of peptides having equimolar amounts of each residue is prepared by adjusting the concentration of each amino acid in the reaction solution based on its relative coupling constant. Those relative coupling constants were determined by completely reacting the twenty naturally occurring resin-linked amino acids with each of the same twenty amino acids. The separate 400 resulting dipeptides were severed from their resins and the amount of each amino acid that coupled was determined.

Upon determining those 400 amounts, the 400 corresponding relative rate constants were determined. The concentrations of the reactants were then adjusted to obtain equimolarity of coupling using an algorithm said to be not straightforward to calculate so that the affects of the previously bonded residue (acceptor) on the incoming amino acid can be taken into account.

In practice, acceptors of similar reactivities are reacted with appropriate mixtures of amino acids to achieve the desired results. The concentrations of reactant amino acids are then adjusted based on the condensation results obtained. Acceptors of differing coupling rates were said to be used in separate reaction mixtures.

U.S. Pat. No. 5,010,175 describes preparation of several pentapeptides said to have a single residue at one or more positions and mixtures of four residues at other positions. The mixed positions were reported to contain their mixed residues at equimolarity plus-or-minus (±) about 20 to about 24 percent.

A study using a mixture of the N-protected naturally occurring amino acids was also reported. The amounts of N-protected amino acids used were based on their relative rate determinations, and adjusted to approximate first-order kinetics by having each amino acid in at least 10-fold excess over its final product. Relative rates were determined by averaging values from the 400 separate reactions and additional data not provided. A table of amounts of each of the twenty N-protected naturally occurring amino acids said to provide equimolarity when used as a mixture is also provided in this patent.

In addition, Furka et al., (1988, 14th International Congress of Biochemistry, Volume 5, Abstract FR:013) and (1988, Xth International Symposium on Medicinal Chemistry, Budapest, Abstract 288, p. 168) described the synthesis of nine tetrapeptides each of which contained a single residue at each of the amino- and carboxy-termini and mixtures of three residues at each position therebetween. Those mixture positions were obtained by reacting resin-linked peptides of the same sequence with different amino acids. The reacted, lengthened resin-linked peptides were then physically mixed to provide the equimolarity. The abstract further asserts that those authors' experiments indicated that a mixture containing up to 180 pentapeptides could be easily synthesized in a single run. No biological assays were reported. More recently, Furka et al., *Int. J. Peptide Protein Res.*, 37:487–493 (1991) reported on the synthesis of mixtures of 27 tetrapeptides and 180 pentapeptides prepared by physically mixing reacted resin-linked peptides. Those peptides were synthesized with one or mixtures of three or four residues at each position along the chain. No biological results using those relatively simple mixtures were reported.

More recently, Huebner et al. U.S. Pat. No. 5,182,366 described a substantially similar physical mixture process. Huebner et al. data provided for a mixture of tetramers having a glycine at position 2 from the amino- (N-) terminus and each of five different amino acid residues at positions 1, 3 and 4 from the N-terminus indicated that each of the residues at positions 1, 3 and 4 were present in substantially equimolar amounts and that glycine was present in its predicted amount. Similar data were also provided for twenty-five groups of pentamers, each of which had two known residues at the amino-termini and mixtures of five residues each at the remaining positions. No data were presented as to biological activity or actually obtaining any selected peptide from the prepared mixtures.

A similar approach was also reported by Lam et al., *Nature*, 354:82–84 (1991). Those workers reported the preparation of millions of bead-linked peptides, each bead being said to contain a single peptide. The peptide-linked beads were reacted with a fluorescent- or enzyme-labeled acceptor. The beads bound by the acceptor were noted by the label and were physically removed. The sequence of the bound peptide was analyzed.

Recent reports (Devlin et al., *Science*, 249:404–405 [1990] and Scott et al., *Science*, 249:386–390 [1990]) have described the use of recombinant DNA and bacterial expression to create highly complex mixtures of peptides. More recently, Fodor et al., *Science*, 251:767–773 (1991), described the solid phase synthesis of thousands of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, Fodor et al. reported preparation of an array of 1024 different peptides coupled to the slide in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a solid phase-bound mixture of peptides sometimes referred to as a combinatorial library is the inability of the peptides generated in those systems to interact in a "normal" manner with acceptor sites, analogous to natural interaction processes (i.e., free in solution at a concentration relevant to the receptors, antibody binding sites, enzyme binding pockets, or the like being studied without the exclusion of a large percentage of the possible combinatorial library), as well as the difficulties inherent in locating one or more active peptides. Secondarily, the expression vector systems do not readily permit the incorporation of the D-forms of the natural amino acids or the wide variety of unnatural amine acids which would be of interest in the study or development of such interactions.

Houghten et al., *Nature*, 354:84–86 (1991) reported use of physical mixtures in a somewhat different approach from those of Furka et al., Huebner et al. and Lam et al., supra, by using solutions of free peptide mixture libraries or sets that overcomes several of the problems inherent in the above art. Here, 324 exemplary hexamer mixtures that contained more than 34 million peptides were first prepared whose N-terminal two positions were predetermined residues, whereas the four C-terminal positions of the sets were equimolar amounts of eighteen of the twenty natural (gene-coded) L-amino acid residues. Binding studies were carried out using those 324 mixtures to determine which few provided optimal binding to a chosen receptor such as a monoclonal antibody or live bacterial cells. That study determined the two N-terminal optimal binding residues.

Another eighteen sets were then prepared keeping the optimal first two optimal binding residues, varying the third position among the eighteen L-amino acids used, and keeping the C-terminal three positions as equimolar mixtures. Binding studies were again carried out and an optimal third position residue was determined. This general procedure was repeated until the entire hexamer sequence was determined.

Similar studies are also reported in Pinilla et al. *Vaccines 92*, Cold Spring Harbor Laboratory Press, Cold Spring Harbor, pages 25–27 (1992); Appel et al., *Immunomethods*, 1:17–23 (1992); Houghten et al., *BioTechniques*, 13:412–421 (1992); Houghten et al., in *Innovation and Perspectives in Solid Phase Syntheses: Peptides. Polypeptides and Oligonucleotides*, R. Epton (ed.), Intercept, Ltd., Andover, pages 237–239 (1992); Houghten et al., in *Peptides*, J. A. Smith and J. E. Rivier (eds.), Proceedings of the Twelfth American Peptide Symposium, ESCOM, Leiden, pages 560–561 (1992); and WO 92/09300 published Jun. 11, 1992.

A still different approach was reported in Pinilla et al., *BioTechniques*, 13:901–905 (1992). In that report, a total of 108 free hexamer peptide mixture sets were prepared. Those sets contained one of eighteen amino acid residues at each of the six positions of the hexamer chains, with the other five positions being occupied by equimolar amounts of those same eighteen residues. Again, over 34 million different peptides were represented by those 108 sets (6 positions×18 residues/position).

Each of the sets was assayed for binding to a monoclonal antibody as receptor. The residue at each position that provided best binding results for that position provided a peptide sequence that was identical to the known epitope for that monoclonal. This process also provided sequences for other peptides that were bound almost as well by the monoclonal.

More recently still, Horton et al., *Proceedings of the 13th American Peptide Symposium,* R. Hodges, ed., ESCOM, (1994), in press, Abstract LF3 (June 1993) described the synthesis of cystine cross-linked peptide mixtures. Those cross-linked mixtures were prepared from a pentamer mixture and a hexamer mixture reacted together. The pentamer had a single residue at positions 1 and 2 from the N-terminus, a mixture of three residues at each of positions 3 and 4, and a cysteine at position 5, the C-terminus. The hexamer had a cysteine at position 1, mixtures of three residues at positions 2 and 5, and single residues at positions 3, 4 and 6. Those two mixtures were oxidized with $I_2$ to form the dimers, 78 out of the theoretical 81 of which were identified. The resulting mixture inhibited angiotensin II binding to the $AT_1$-receptor.

The approach of Horton et al. utilized relatively small mixtures of residues at each position and disclosed no procedure for identifying individual sequences that exhibit enhanced binding. In addition, having the cysteine residues at termini maintained the linearity of the starting peptides.

BRIEF SUMMARY OF THE INVENTION

The present invention contemplates dimeric oligopeptide mixture sets whose members are linked together by a disulfide bond, libraries of such dimers and processes for using those materials.

Thus, a dimeric oligopeptide mixture set is contemplated. Such a set is comprised of dimer molecules having two bonded portions in which the oligopeptide chains of a first oligopeptide portion are bonded by a disulfide bond to the oligopeptide chains of a second oligopeptide mixture portion.

(A) Each oligopeptide in the first oligopeptide portion has (a) a chain that contains the same number of 3 to about 10, and more preferably 4 to about 7, amino acid residues, including an oxidized mercaptan-containing residue, preferably cysteine, that is located at the same position in each oligopeptide chain and forms part of the disulfide bond. The oxidized mercaptan-containing residue is the only mercaptan-containing residue in the chain.

(b) Each portion also has an amino acid residue sequence, in addition to the oxidized mercaptan-containing residue, that contains one of at least six predetermined amino acid residues at the same, one or more predetermined positions of the oligopeptide chain.

In addition, (B) each oligopeptide in the second oligopeptide mixture portion bonded to the first oligopeptide portion has (a) a chain that contains the same number of 3 to about 10, and more preferably 4 to about 7, amino acid residues, including an oxidized mercaptan-containing residue, preferably cysteine, that is located at the same position in each oligopeptide chain and forms a part of the disulfide bond. This oxidized mercaptan-containing residue is the only mercaptan-containing residue present in this chain. The second oligopeptide mixture has equimolar amounts of the at least six different amino acid residues at the same one or more other positions of the oligopeptide chain. The dimeric oligopeptide mixture set is substantially free of oligopeptide molecules having no disulfide bond.

In one preferred embodiment, the second oligopeptide mixture portion is the same as the first oligopeptide portion and the molecules of the dimeric oligopeptide mixture set are homodimers, whereas in another embodiment, the chains of the second oligopeptide mixture portion are different from the chains of the first oligopeptide portion, and the molecules of the dimeric oligopeptide mixture set are heterodimers. A mixture of homodimers and heterodimers is also contemplated.

It is also preferred that each oligopeptide chain of the second oligopeptide mixture portion have an amino acid residue sequence, in addition to the oxidized mercaptan-containing residue, that contains one of at least six, and more preferably at least ten, predetermined amino acid residues at the same, one or more predetermined position of the oligopeptide chain.

It is further preferred that the oxidized mercaptan-containing residue in the first oligopeptide portion and in the second oligopeptide mixture portion be positioned at other than the amino-terminus or carboxy-terminus of each oligopeptide chain.

A library of dimeric oligopeptide mixture sets is also contemplated that comprises a plurality of sets of the above-discussed dimeric oligopeptide mixtures.

Each set of the library has the same length, position of the oxidized mercaptan-containing residue in each chain, and number of chain positions occupied by equimolar mixtures of the same at least six different amino acid residues. Each set in the library differs from the other sets in:

(a) the position of the one or more predetermined amino acid residues in the oligopeptide chain, (b) the identity of the one or more predetermined amino acid residues, or (c) both the position and identity of the one or more predetermined amino acid residues.

The before-mentioned preferences for the individual sets hold also for a library.

A process for determining the sequence of a dimeric oligopeptide ligand that preferentially binds to an acceptor is also contemplated. That process comprises the steps of:

(a) providing a library of dimeric oligopeptide sets as discussed generally before, except that here, each set in the library differs from the other sets in the identity of the one or more predetermined amino acid residues in the oligopeptide chain.

(b) Each set from the library of sets is separately admixed with the acceptor in an aqueous medium at a set concentration of about 0.1 milligrams per liter to about 100 grams per liter, the binding of each set to the acceptor is separately assayed, and a set exhibiting preferential binding relative to the other sets is determined, thereby identifying an amino acid residue that provided preferential binding at the one or more predetermined positions.

(c) A second library of sets is provided that is identical to the first library except that each oligopeptide chain has (i) the amino acid residue identified in step (b) at the one or more predetermined positions and (ii) a predetermined one of the at least six different amino acid residues at another predetermined position of the oligopeptide chain that is different from the one or more positions of the identified amino acid residue of the first-named library of sets. The second library of sets has equimolar amounts of each of the at least six different amino acid residues of the first-named sets at the same one or more positions of the dimeric oligopeptide chains not occupied by the identified amino acid residue(s) or predetermined amino acid residue(s).

(d) Each set of the second library of sets is separately admixed with the acceptor in an aqueous medium at a set concentration of about 0.1 milligrams per liter to about 100 grams per liter, the binding of each set to the acceptor is separately assayed, and a second set exhibiting preferential binding is determined, thereby identifying an amino acid residue that provides preferential binding at the other predetermined position in the oligopeptide chain.

(e) Steps (c) and (d) are repeated using zero through fifteen further libraries of sets of dimeric oligopeptide mixture sets instead of the second library of sets or until preferential binding does not increase when a further library is assayed. Each further library of sets of dimeric oligopeptide mixture sets comprises a mixture of equimolar amounts of member dimeric oligopeptide chains containing the same number of amino acid residues in each dimeric oligopeptide chain as the chains of the first-named library of sets. The member chains of the sets of each further library contain the amino acid residues in the dimeric oligopeptide chain positions that exhibited preferential binding in a library of sets used immediately before, and a predetermined one of the at least six different amino acid residues at another predetermined position of the dimeric oligopeptide chain different from the positions of the identified amino acid residues of the library of sets used immediately before. Each of the further library of sets has equimolar amounts of the at least six different amino acid residues of the first-named sets at the same one or more positions of the oligopeptide chain not occupied by the identified amino acid residues or the predetermined amino acid residues.

(f) Where the last-assayed library of sets exhibits increased preferential binding compared to the library used immediately before and one position of the dimeric oligopeptide chain that provides preferential binding is not identified, at least six dimeric oligopeptide chains are provided in which each chain contains the same number of amino acid residues in each dimeric oligopeptide chain as the chains of the first-named plurality of sets, each dimeric oligopeptide chain contains the identified amino acid residues in the oligopeptide chain positions that exhibited increased preferential binding in the immediately preceding assay of step (e) and a predetermined one of the at least six different amino acid residues at another predetermined position in the dimeric oligopeptide chain different from the positions of the identified amino acid residues used in the immediately preceding assay of step (e).

(g) Each of the at least six dimeric oligopeptides of step (f) is separately admixed with the acceptor in an aqueous medium at a dimeric oligopeptide concentration of about 0.1 milligrams to about 100 grams per liter, is separately assayed for the binding of each dimeric oligopeptide, and the dimeric oligopeptide that exhibits preferential binding is determined, thereby determining the sequence of a dimeric oligopeptide ligand that preferentially binds to the acceptor.

It is preferred in this process that the identified and predetermined amino acid residues be adjacent residues.

Another process for determining the sequence of a dimeric oligopeptide ligand that preferentially binds to an acceptor is also contemplated. This process comprises the steps of:

(a) providing a library of oligopeptide mixture sets as discussed generally before, in which each set of this library differs from the other sets in the identity and chain position of a single predetermined amino acid residue of the at least six different residues at the predetermined position within the set, and in which each chain position of difference is occupied by an equimolar mixture of at least six different residues when it is not occupied by a predetermined residue.

(b) Each set is separately admixed with the acceptor in an aqueous medium at a set concentration of about 0.1 milligrams per liter to about 100 grams per liter, and the binding of each set to the acceptor is separately assayed.

The amino acid residue that exhibited preferential binding at each position of the oligopeptide chain of each set that differed from the other sets provides the sequence of a dimeric oligopeptide that preferentially binds to the acceptor.

DETAILED DESCRIPTION OF THE INVENTION

Dimer Oligopeptide Mixture Sets

The present invention contemplates a mixture of two-portion oligopeptide molecules that is referred to herein as a dimeric oligopeptide mixture set, and the use of those molecules as biologically active ligands that can be used to determine the complete sequence of a dimeric oligopeptide ligand. Specific, individual oligopeptide dimers are also contemplated.

The contemplated molecule sets are dimeric oligopeptides comprised of amino acid residues linked together by peptide bonds and are referred to as a "set" because the individual dimeric oligopeptide molecule members of each set are related by amino acid residue sequence, length (or size), terminal substituents and structure. The contemplated sets are referred to as being a "mixture" because at least one portion of each oligopeptide dimer set is itself an equimolar mixture of oligopeptides so that the whole set contains a mixture of molecules. The molecules are referred to as "dimeric" or "dimers" because each molecule contains first and second oligopeptide portions or parts connected by a disulfide bond formed from two oxidized mercaptan-containing residues such as that of a cystine residue formed between an oxidized cysteine (Cys) residue present in each part of the molecule. That oxidized mercaptan-containing (e.g. cysteine) that links the two portions of the dimer molecule is the only mercaptan-containing residue present in the oligopeptide chains.

The oxidized mercaptan-containing residue can be a D- or L-amino acid residue, and the D-isomer can be present in one portion of the dimeric molecule whereas the L-isomer is present in the other portion. The isomer used is, however, held constant within each portion. The L-isomer is utilized illustratively herein.

The mercaptan-containing residue is preferably a cysteine residue. However, the use of homocysteine, penicillamine and the like is also contemplated in place of cysteine in one or both portions of the molecule. One portion of the molecule can therefore contain a cysteine residue, whereas the other portion contains a homocysteine so that a mixed disulfide is formed on oxidation to connect both oligopeptide portions of the molecule.

Although other mercaptan-containing amino acid residues can be used herein, cysteine is often used illustratively herein. In addition, for ease of understanding, phrases such as "cysteine", "oxidized cysteine", "cystine" and the like are often used rather than a more general phrase such as "mercaptan-containing residue" and "oxidized mercaptan-containing residue". It is to be understood, however, that except where a cysteine residue or cystine is specifically recited in a sequence, the more general meaning is intended.

The present invention is usually described in a preferred embodiment in which the dimeric oligopeptide mixture sets, their precursor oligopeptides and ultimately produced dimeric oligopeptide ligands are prepared from most or all of the twenty naturally occurring L-amino acid residues. It should be understood, however, that the invention can be used with at least six different amino acid residues, and with more than twenty different residues.

For instance, a dimeric oligopeptide mixture set can include the naturally occurring 20 amino acids, one or both isomers of ornithine, norleucine, hydroxyproline, β-alanine and the other $C_4$–$C_6$ amino acids such as γ-aminobutyric and ε-aminocaproic acids and the D-stereoisomers of the naturally occurring twenty amino acids, so that use of about fifty D- and L-amino acids is contemplated for synthesis. Those about fifty amino acids are typically used in N-protected form such as t-BOC, Fmoc or CBZ during synthesis. Precursor oligopeptides that contain all D-amino acid residues and mixtures of both D- and L-forms are contemplated for use in preparing corresponding dimeric oligopeptide mixture sets.

Consequently, as used herein, the term "amino acid" will, unless otherwise stated, be intended to include not only the naturally occurring (genetically coded) L-amino acids but also their D-stereoisomers and unnatural amino acids. The phrases "amino acid derivative", "protected amino acid derivative" or the like are used herein for a protected amino acid added as a reactant, whereas the phrase "amino acid residue", "residue" or the like is used herein for a reacted amino acid that is a portion of an oligopeptide chain.

Further, the terms "peptide" and "oligopeptide" are considered to be synonymous (as is commonly recognized) and each term can be used interchangeably as the context requires. The word "polypeptide" is used for chains containing at least ten amino acid residues. All oligopeptide and polypeptide formulas or sequences shown herein are written from left to right and in the direction from amino-terminus to carboxy-terminus.

The abbreviations used herein for derivatives and residues of the twenty natural amino acids are reproduced in the following Table of Correspondence:

| TABLE OF CORRESPONDENCE | | |
|---|---|---|
| Abbreviation | | |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A dimeric oligopeptide mixture set thereof similarly contains a before-defined amino acid residue whose identity is known or specifically defined.

A "predetermined position" in an oligopeptide sequence or chain is a position, from and including the amino-terminal residue as position 1, occupied by a predetermined amino acid residue or an equimolar mixture of at least six residues, and which position is known and specifically identified.

The letter "O" is used herein to indicate a predetermined, but unspecified single amino acid residue of an oligopeptide of a precursor, a dimeric oligopeptide mixture set or portion thereof. Subscripted letters "O", e.g., $O_1, O_2, O_3, \ldots O_n$ etc. indicate a predetermined amino acid residue that is predetermined (specified) and at the same position (1, 2, 3 ... n) among a set of precursor oligopeptides, in a dimeric oligopeptide mixture set, or portion thereof. Thus, a subscripted letter "O" such as $O_1$ is used where a particular amino acid residue is intended such as alanine or leucine, whereas an unsubscripted letter "O" is used to mean that each of the plurality of at least six individual residues is present at a given position, but that residue while not being specified, is a single residue. Subscripted numbers need not start at the amino-terminus for any given chain.

The letter "X" is used to indicate that a position in a dimeric oligopeptide mixture set, a portion thereof, or precursor oligopeptide set formula occupied by that letter is an equimolar mixture of each of at least six amino acid residues, and preferably ten or more such residues, and more preferably about 15 to about 20.

A contemplated oligopeptide mixture set is comprised of dimer molecules having two bonded portions in which the oligopeptide chains of a first oligopeptide portion (or first portion) are bonded by a disulfide bond to the oligopeptide chains of a second oligopeptide mixture portion (or second portion). Thus, the oligopeptide chains of the first oligopeptide portion are individually disulfide-bonded (e.g., cystine-bonded) to individual oligopeptide chains of the second portion mixture of oligopeptides. Because one portion must contain a mixture, the set contains a mixture also. The oxidized cysteine residues that link the two portions of the molecule together are the only cysteine residues present in a contemplated dimer molecule.

Each oligopeptide chain in a first oligopeptide portion has (a) a chain that contains the same number of 3 to about 10 amino acid residues so that each oligopeptide chain of that first mixture is the same length. That chain length includes an oxidized cysteine residue that is located in the same position in each oligopeptide chain and forms part of the cystine that bonds the two portions of the molecule together.

Each oligopeptide chain of that first oligopeptide portion also has (b) an amino acid residue sequence that contains one of at least six predetermined amino acid residues at the same at least one (one or more) predetermined position of the oligopeptide chain other than that occupied by the oxidized cysteine residue. Thus, in addition to the oxidized cysteine residue whose position is predetermined and constant for each member chain in a first oligopeptide portion, each chain also contains at least one amino acid residue whose identity and position in the chain are predetermined and constant for all oligopeptide chain members of the mixture. That at least one residue is one of at least six preselected residues, and is more preferably one of at least 10 residues, and is most preferably one of about 15 to about 20 residues. A first oligopeptide portion, aside from the oxidized cysteine, thus has at least one sequence position specifically defined. The remaining chain position(s) of the first oligopeptide portion can be occupied by other single residues of those at least six different residues, or equimolar mixtures thereof as discussed below.

In preferred practice, a first oligopeptide portion additionally includes one or more chain positions that are occupied by an equimolar mixture of at least six different amino acid residues so that as an entity, including all of the peptides, the first oligopeptide portion is a mixture referred to herein as a first oligopeptide mixture portion. A preferred first oligopeptide mixture portion therefore has three positions that are defined, although not necessarily specified: one position in each chain contains the specified oxidized Cys, another position contains the specified same single one of at least six residues, and the third defined position has an equimolar mixture those same at least six residues when all of the oligopeptides of this portion are viewed together. The remaining sequence position(s), when present, of such a mixture can be occupied by the same or another single residue(s) of those at least six different residues, can be occupied by an equimolar mixture(s) of those at least six residues or can be occupied both by one single, specified residue at one or more predetermined positions and mixtures at other predetermined positions.

For example, using a mixture prepared using the 20 naturally occurring amino acids except cysteine in which the amino-terminal residue is a predetermined residue $O_1$ that is one of those 19 residues such as alanine, position 2 from the N-terminus is occupied by the oxidized Cys residue, C, and the third position is occupied by an equimolar amount of the 19 residues, X, an exemplary first oligopeptide mixture can be depicted by the formula $O_1CX$. That formula represents a mixture of 19 different oligopeptides ($1\times1\times19$). A tetramer whose amino-terminal two positions are as above and whose carboxy-terminal positions are occupied by mixtures contains 361 different oligopeptides ($1\times1\times19\times19$). A similarly prepared heptamer mixture whose N-terminal first two positions are as above and whose remaining five positions are occupied by equimolar amounts of those 19 naturally occurring amino acid residues contains about 2.5 million different oligopeptide chains ($1\times1\times19\times19\times19\times19\times190=1\times19^5$).

The oligopeptide chains of the first oligopeptide portion are disulfide-bonded to chains of a second oligopeptide mixture portion. The chains of the second oligopeptide mixture portion (a) each have the same length of 3 to about 10 amino acid residues, including the oxidized mercaptan-containing residue that forms part of the disulfide and that is present at the same position in each oligopeptide chain of this mixture portion.

The second oligopeptide mixture portion as an entity; i.e., all of those portions together, has equimolar amounts of the before-noted at least six different amino acid residues at the same at least one (one or more) other chain position in addition to that occupied by the oxidized cysteine. It is more preferred that the position of equimolarity be occupied by at least 10, and most preferably by about 15 to about 20 different amino acid residues. The remaining position(s) of the second oligopeptide mixture portion can be occupied by single residues or equimolar mixtures, as noted before.

Where the above at least one constant sequence position of a first oligopeptide portion is occupied by an Ala, Val, Ile, Gly, Ser or Thr residue, the mixture of the second oligopeptide portion contains equimolar amounts of oligopeptide chains that have those same residues at a chain position other than that of the oxidized cysteine that is the same for each chain. Similarly, where the above first portion predetermined, constant sequence position is occupied by one of at least 10 residues, the one or more mixture position of the second portion contains equimolar amounts of oligopeptide chains containing the same at least 10 residues at another position in the chains. The same holds where one of about 15 to about 20 residues is used for the predetermined position of the first portion. Looked at differently, the one, single, predetermined residue at the same one or more (at least one) positions of the oligopeptide chains is one of the residues used at the mixture position(s).

Thus, in one embodiment, each of the oligopeptide chain positions of a second oligopeptide mixture portion other than that occupied by the mercaptan-containing residue is occupied by equimolar amounts of the residues used for the mixture positions, with those residues being the same residues used for the mixture positions of a preferred first oligopeptide portion, and includes the one residue at the predetermined position of that first portion chain. Using a 4-mer mixture as exemplary of a second oligopeptide mixture portion, in which the first, N-terminal, position is occupied by a mixture of the 19 of 20 naturally occurring amino acid residues, X, the second position is occupied by the oxidized Cys, C, and the third and fourth positions are also mixtures of those same 19 residues, a second oligopeptide mixture portion can be represented by the formula XCXX; SEQ ID NO:1. The formula of SEQ ID NO:1 represents an equimolar mixture of 6859 oligopeptide chains ($19\times1\times19\times19$). The oligopeptide portion of SEQ ID NO:1 can also be expressed as Xaa-Cys-Xaa-Xaa, in which Xaa is an equimolar mixture of at least six different amino acid residues that are free of mercaptan groups.

In more preferred embodiments, each oligopeptide chain of a second oligopeptide mixture portion also has (b) an amino acid residue sequence that contains one of at least six predetermined amino acid residues at the same at least one position of the oligopeptide chain other than those occupied by the oxidized cysteine residue and the position in each chain that is a mixture position. That at least one residue that can be one of at least six preselected residues, is more preferably one of at least 10 residues, and is most preferably one of about 15 to about 20 residues, and those at least six, at least 10 or about 15 to about 20 residues are the same as those used in the first oligopeptide portion for selection of the predetermined residue whose identity and position in the chain are constant within the mixture.

To reiterate, one oligopeptide portion of a contemplated dimeric oligopeptide mixture set has a single predetermined residue at a predetermined chain position. That portion is referred to herein as a first oligopeptide portion. The other oligopeptide portion has a mixture of oligopeptides at at least one chain position and is referred to as a second oligopeptide or a second oligopeptide mixture. The dimeric oligopeptide mixture set must have at least one position in one portion that contains an equimolar mixture of residues and that portion is referred to as the second oligopeptide mixture portion.

It is to be understood that as was the case with the first oligopeptide portion, the second oligopeptide mixture portion can also have one or more position of its chains occupied by a predetermined (known) residue. The first oligopeptide portion and second oligopeptide portion can be broadly defined as being the same. As is discussed hereinafter, the first and second oligopeptide mixtures can be the same in a dimeric oligopeptide mixture set.

The above designations of "first" and "second" are thus made for ease of understanding in describing the contemplated subject matter and have no other significance, inasmuch as a homodimer contains two portions that have the same predetermined residues at the same at least one predetermined position, an oxidized cysteine at the same position in each chain, and equimolar mixtures at the same at least one other position.

The chains of the first oligopeptide portion can have a length of 3 to about 10 residues, as can the chains of a second oligopeptide mixture portion. It is to be reiterated that the chain lengths of each portion are the same for the oligopeptides of that portion. It is to be noted, however, that the length of the chains of the first portion of a dimeric molecule is independent of the length of chains in the second portion. Thus, the chains of a first oligopeptide portion can have a length of three residues, whereas the chains of a second oligopeptide mixture portion are ten residues long. It is preferred, however, that the chain length be the same for both the chains of a first oligopeptide portion and a second oligopeptide mixture portion. It is also preferred that the chain length for either portion be 4 to about 7 residues.

The oxidized cysteine (mercaptan-containing) residue in either portion of a dimer molecule can be at any position along the oligopeptide chain and can be in different chain positions relative to the amino-terminus (N-terminus) or carboxy-terminus (C-terminus) in each portion of the molecule. Thus, in one embodiment, the oxidized cysteine of the chains of the first oligopeptide portion can be at the N-terminus, whereas the oxidized cysteine of the chains of the second oligopeptide mixture portion are at the C-terminus.

In some preferred embodiments, that oxidized cysteine is at the same position in the chains from the N-terminus for both the first oligopeptide portion, and second oligopeptide mixture portion. It is also preferred that at least one and more preferably both oxidized cysteine residues be positioned at other than the N-terminus or the C-terminus in both portions. Such non-terminal cystine bonding provides greater tertiary structure to the dimers than is possible when one or both oxidized cysteines are at a terminus.

In another embodiment, the mercaptan-containing entity is at the amino-terminus and is a $C_2$–$C_4$ mercaptocarboxylic acid residue ($C_2$–$C_4$ mercaptoacyl residue or group). That is, a $C_2$–$C_4$ mercaptocarboxamide group is present that includes the nitrogen atom of the α-amine of the N-terminal amino acid residue. The terminal $C_2$–$C_4$ mercaptocarboxamide is treated herein as if it contained an amino group and were an amino acid residue. The mercapto group of this residue is used to form one or both portions of the disulfide bond that links the two oligopeptide portions together. Exemplary $C_2$–$C_4$ mercaptocarboxylic acids include thioglycolic (mercaptoacetic), 2- and 3-mercaptopropionic and 4-mercaptobutyric acids.

The first oligopeptide portion as an entity preferably contains equimolar amounts of at least six different amino acid residues at the same at least one position in its collective oligopeptide chains. The identities of those mixture position at least six residues are the same as those from which are selected the single predetermined amino acid residues that are present at one or more (at least one) predetermined positions in the oligopeptide chain. Thus, if one of Gly, Ala, Val, Ile, Ser or Thr is at the same predetermined position of all of the chains, one-sixth of those preferred chains also contain each of Gly, Ala, Val, Ile, Ser and Thr at another predetermined chain position that is the same for all chains so that each of those latter residues is present at the same position in the mixture, and the entire mixture contains equimolar amounts of those six residues at that chosen chain position.

A second oligopeptide mixture portion must have equimolar amounts of at least six amino acid residues at a predetermined chain position, and the residues present at that position of equimolarity are the same as those from which the predetermined residue in the first oligopeptide portion is selected. Using the residues above as exemplary for the first oligopeptide portion, one-sixth of the chains of the second oligopeptide mixture portion contain each of Gly, Ala, Val, Ile, Ser and Thr at the same chain position.

It is thus seen that the predetermined residue other than cysteine of a first oligopeptide mixture portion that is present at the same, predetermined position in each chain is one of the residues that is present in equimolar amounts at another chain position for that portion as well as being one of the residues present in equimolar amounts in the chains of the second oligopeptide mixture portion.

In more preferred practice, the residue other than cysteine at the same predetermined position of all of the oligopeptide chains of the first oligopeptide portion is one of at least 10, and most preferably about 15 to about 20 residues. The equimolar mixture positions of the first oligopeptide portion and second oligopeptide mixture portion therefore also more preferably contain the same at least 10, and most preferably contain the same about 15 to about 20 residues.

As is discussed in greater detail hereinafter, the N-terminal amino group of each residue of each chain in either portion of a dimeric oligopeptide molecule can be a free amine or can be bonded to a $C_1$–$C_{18}$ straight or branched chain acyl group, or a pyroglutamoyl group. An acetyl group is preferred. Of course, when the terminal "residue" is a $C_2$–$C_4$ mercaptocarboxamide, no other N-terminal group is present.

The C-terminal residue of each chain in either portion of a dimer oligopeptide molecule can be a carboxyl (or carboxylate depending on pH value) or a carboxamido (amide) group. Use of a C-terminal amide is preferred. It is particularly preferred that the N-terminal residue in the chains of both portions of the molecule be bonded to an acetyl group and the C-terminal residue of each chain in both portions be an amide.

The dimeric molecules can themselves be "homodimers" in which the oligopeptide chains of one oligopeptide mixture portion are linked together by the disulfide, or those molecules can be "heterodimers" in which the oligopeptide chains of one oligopeptide portion are disulfide-bonded to the oligopeptide chains of a different oligopeptide portion. Thus, for example, if a first oligopeptide portion were the oligopeptide mixture A, and a second oligopeptide mixture portion were the oligopeptide mixture B, one contemplated homodimer oligopeptide mixture set can be depicted A—A and another B—B, with the heterodimer mixture set being depicted A-B, the depiction B-A being redundant of A-B.

A contemplated oligopeptide mixture set can thus contain heterodimers, homodimers or both hetero- and homodimers. The make-up of the dimers present is a function of both portions of the molecule as well as the technique used for joining both portions together, as is discussed hereinafter.

Regardless of what type of dimers are present, a contemplated dimeric oligopeptide mixture set is substantially free of oligopeptide molecules that have no disulfide bond. Thus, whereas some previously prepared oligopeptide mixtures may inadvertently have had a few percent dimeric, disulfide-containing oligopeptide molecules in a mixture containing more than 90 percent monomeric oligopeptide molecules free of such disulfide bonds, dimeric oligopeptide mixtures such as those contemplated here have at most a few percent of oligopeptides containing no disulfide bond.

Preparation of Dimer Mixtures

Dimer molecule preparation will be discussed in terms of embodiments in which a precursor first oligopeptide mixture portion and a precursor second oligopeptide mixture portion are reacted together. The preparation of dimer molecules prepared from a single sequence precursor first oligopeptide portion and a precursor second oligopeptide mixture portion is substantially identical to that above, except there are fewer reactant peptides present.

The preparation of precursor linear oligopeptide mixtures having a predetermined residue at at least one position and preferably having equimolar amounts of at least six other desired residues at one or more (at least one) other positions begins with the preparation of a corresponding precursor oligopeptide mixture. Equimolarity being of importance for the residues of the mixture positions, synthesis of the precursor oligopeptide mixtures is of importance.

Two general approaches to such syntheses are preferred. One is referred to as the physical mixture process and the other is referred to as the chemical mixture process.

The physical mixture process utilized is that described in Houghten et al., *Nature*, 354:84–86 (1991); Pinnila et al., *Vaccines* 92, Cold Spring Harbor Laboratory Press, Cold Spring Harbor, pages 25–27 (1992); Appel et al., *Immunomethods*, 1:17–23 (1992); and WO 92/09300 published Jun. 11, 1992. These synthetic processes are also similar to the processes disclosed in Furka et al., *Int. J. Peptide Protein Res.*, 37:487–493 (1991), Huebner et al. U.S. Pat. No. 5,182,366, incorporated by reference, and Lam et al., *Nature*, 355:82–84 (1991).

The latter two processes and that used for preparing precursor oligopeptide mixtures herein differ in concept. In both Lam et al. and Huebner et al., the desired peptide is selected by its binding or reaction, recovered and then its sequence is determined. Furka et al. teach no reactions with their mixtures.

A chemical mixture synthesis of precursor oligopeptide mixtures can be one of those described in Rutter et al. U.S. Pat. No. 5,010,175 or Geysen U.S. Pat. No. 5,194,392, whose disclosures are incorporated by reference, or as described in the previously noted published papers of which Geysen is an author, except that Geysen's U.S. Pat. No. 5,194,392 does not teach cleavage from the solid support, and cleavage of an oligopeptide mixture is required herein.

Both Rutter et al. and Geysen report using N-t-BOC protecting groups for their chemical mixture syntheses. Each of those patents provides a different exemplary mixture of N-t-BOC-blocked amino acid derivatives for use in synthesis of equimolar amounts of amino acid residues.

It is noted that the present invention is not limited to use of N-t-BOC blocking groups for synthesis of precursor oligopeptides. This is the case whether the physical or chemical mixture approaches are utilized. Thus, any blocking group can be utilized. Table 1, below, provides mole ratios of blocked amino acids that can be used for a chemical mixture synthesis using Fmoc blocking group chemistry.

TABLE 1*

| Amino Acid | Mole Ratio |
| --- | --- |
| Ala | 0.22 |
| Asp(tBu ester) | 0.47 |
| Glu(tBu ester) | 0.62 |
| Phe | 0.35 |
| Gly | 0.20 |
| His(Tr) | 0.72 |
| Ile | 2.51 |
| Lys(tBoc) | 0.59 |
| Leu | 0.48 |
| Met | 0.34 |
| Asn | 1.65 |
| Pro | 0.20 |
| Gln | 2.03 |
| Arg(Mtr) | 1.98 |
| Ser(tBu ether) | 0.80 |
| Thr(tBu ether) | 2.18 |
| Val | 1.85 |
| Tyr(tBu ether) | 0.81 |
| Trp | 0.99 |

*Parenthesized designations in the left column are protecting groups. tBu = t-butyl; Tr = trityl; tBoc = t-butyloxycarbonyl; Mtr = 4-methoxy-2,3,6-trimethylbenzenesulfonyl.

Equimolarity in the mixture positions is typically within the limits of weighing accuracy using the physical mixture synthetic process because single amino acids are reacted in large excess and reactions are driven to completion. The chemical mixture process does not provide exact equimolarity as does the physical mixture process. For example, U.S. Pat. No. 5,010,175 reported variation from equimolarity in the range of 0.20–0.32 moles and an average of 0.25±0.04, with each amino acid being no more than 0.8 to 1.28 times the desired result. Deviations from equimolarity from that obtained with the physical mixture method of up to about 35 percent have been observed with no adverse effect. Regardless of the deviations from exact equimolarity observed from use of the chemical mixture method, the various oligopeptides required to obtain enhanced binding by a corresponding oligopeptide mixture portion of a dimer molecule mixture are present in large enough quantities to be useful in the assay methods discussed hereinafter.

It is thus seen that both physical and chemical mixture synthetic processes for preparing a desired precursor oligopeptide set are well known in the art. Use of a physical mixture method is preferred and is discussed in Example 1, hereinafter.

It is reiterated that a contemplated dimer contains only two oxidized mercaptan-containing residues so that cysteine or other mercaptan-containing residue other than that used to form the disulfide bond is omitted from an oligopeptide mixture. Tryptophan is frequently omitted from such mixtures and the corresponding dimer oligopeptide mixture sets because of side reactions that can occur from its use. It has been found, however, that use of an N-formyl blocking group on tryptophan can alleviate much of the difficulty in synthesis when that residue is incorporated into an oligopeptide chain. $N_\alpha$-t-BOC-N-Formyl tryptophan is available from Bachem, Inc., Torrence, Calif.

In preferred practice, each oligopeptide is coupled to the solid support during synthesis by a selectively severable covalent bond, such as an ester or an amide bond. An ultimately produced precursor oligopeptide mixture can be cleaved (separated or severed) from the solid support, recovered and used to form a dimeric oligopeptide mixture set.

A $C_1$–$C_{18}$ straight or branched chain acyl (hydrocarboyl) or pyroglutamoyl group is preferably bonded to the N-terminus of an oligopeptide chain of a precursor oligopeptide mixture so that after deblocking, each member chain of an oligopeptide mixture contains a $C_1$–$C_{18}$ straight or branched chain hydrocarbamide or pyroglutamamide group. An acetyl (acetamide) group, a $C_2$ acyl group, is preferred and is often referred to herein as "Ac". Other exemplary $C_1$–$C_{18}$ acyl groups include formyl, propionyl, butyryl, 2-methylpropionyl, hexanoyl, benzoyl, octanoyl, lauroyl, palmitoyl, oleoyl and stearoyl. Hydrogen can also be present at the amino-terminus of the precursor chains.

A $C_1$–$C_{18}$ acyl or pyroglutamoyl group is added by reaction of a corresponding anhydride such as acetic anhydride, acid halide such as octanoyl chloride, by reaction of a suitable activated ester such as N-hydroxysuccinimidyl benzoate or using the free carboxyl group and a carbodiimide such as DCC. An acyl group is usually added to a solid support-coupled oligopeptide upon removal of the selectively removable blocking (protecting) group, e.g. N-t-BOC or N-Fmoc, from the N-terminal a-amino group.

Where an oligopeptide mixture is synthesized coupled to the solid support by an ester formed from the C-terminal residue via a direct bond or an intermediary linker such as in a PAM resin ester, and a C-terminal amide is desired in the oligopeptide mixture, the oligopeptide mixture can be severed from the solid support by aminolysis using ammonia. Normal cleavage of an ester group-bonded oligopeptide from the solid support using HF results in a C-terminal carboxyl group. Cleavage of an amide-bonded oligopeptide from a benzhydrylamine resin solid support with HF results in the formation of a C-terminal amide group.

Syntheses of precursor oligopeptide mixtures is preferably carried out using foraminous (porous) containers that are described in U.S. Pat. No. 4,631,211, whose disclosures are incorporated by reference. Another useful synthetic technique, particularly for use in the chemical mixture process, is the process described in Lebl et al. U.S. Pat. No. 5,202,418, whose disclosures are incorporated herein by reference.

Various useful solid supports, methods of their use, reagents for linking the growing oligopeptide to the support, cleaving an oligopeptide from the support and the like are well known to workers skilled in this art such that further exemplification is unnecessary. Further such exemplifications can, however, be found in U.S. Pat. No. 4,631,211 and in WO 92/09300, published Jun. 11, 1992, whose disclosures are incorporated by reference.

A precursor oligopeptide other than a single, specified sequence can be a mixture that comprises equimolar amounts of oligopeptide chains that contain the same number of amino acid residues in each chain; i.e., have the same chain length of 3 to about 10 residues, and more preferably about 4 to about 7 residues. The amino-terminus of each of the oligopeptides in the mixture is amino, a $C_1$–$C_{18}$ hydrocarboylalkylamido or a pyroglutamoyl group, and the carboxy-terminus is an amido or a carboxyl group. Those N- and C-terminal groups are also present in the diner oligopeptide mixture molecules.

A preferred precursor oligopeptide mixture has one or more (at least one) predetermined (specifically defined) amino acid residues at the same one or more (at least one) predetermined (specifically defined) positions of the oligopeptide chain and equimolar amounts of at least six different amino acid residues, more preferably at least ten different residues, and most preferably about 15 to about 20 different amino acid residues, at one or more (at least one) predetermined (specifically defined) other positions of the chain, the one or more predetermined residues being one of the at least six different residues present in equimolar amounts. When more than one predetermined amino acid residue is present at more than one predetermined position of the chain, those residues can be the same of different.

The number of amino acid residues for the equimolar mixture positions, and thus the number of different sets, is at least six, and more preferably at least ten. Most preferably, that number is about 15 to about 20. It is often preferred to use 18 (t-BOC-synthesized) or 19 (Fmoc-synthesized or t-Boc-N-formyl Trp) sets for each library; i.e., the naturally occurring 20 amino acids are often used except cysteine, and sometimes tryptophan that can be difficult to couple and can also cross-link.

A preferred precursor oligopeptide mixture contains the one or more predetermined residues at one or more predetermined positions that include a chain terminus, most preferably the N-terminus. Such a precursor mixture also preferably includes an equimolar amount of at least six different amino acid residues at one or more predetermined chain positions. Chain mixture positions are preferably adjacent to one another. In particularly preferred practice, those adjacent equimolar mixture positions are at a terminus of the oligopeptide chain that is most preferably the C-terminus. The same mixture of residues is present at each predetermined mixture position.

In other embodiments, the N-terminal two residues of a precursor oligopeptide are predetermined residues within the mixture, the N-terminal three residues are predetermined, or the N-terminal four residues are predetermined when a mixture is six residues long or longer, with the other positions occupied by equimolar mixtures of residues. Thus, one or more predetermined chain positions at a preferred precursor oligopeptide N-terminus are preferably occupied by predetermined residues and one or more chain positions at the C-terminus are occupied by an equimolar mixture of residues, with the cysteine being therebetween.

For a precursor oligopeptide six residues long or longer, an exemplary oligopeptide mixture contains one cysteine (mercaptan-containing residue) at the same position in each chain, and at least one other position, and preferably more than one other position, of the chain of such a precursor oligopeptide mixture is occupied by a predetermined amino acid residue whose identity is the same at the same position within the chain for each mixture, and that one or more predetermined amino acid residue is most preferably at an amino-terminal position of the chain, including the amino-terminus of the chain. It is to be understood that although the identity of each predetermined residue at a given position in the chain is the same within each mixture, each such chain position can be occupied by the same or a different residue as between mixtures. A preferred precursor oligopeptide mixture also contains equimolar amounts of at least six different amino acid residues at the carboxy-terminal 1, 2, 3, 4 or 5 positions of the oligopeptide chain (i.e., positions 6, 5, 4, 3 or 2 from the amino-terminus of a 6-mer), as specifically defined position(s).

Exemplary precursor oligopeptide mixtures include a tripeptide having one predetermined position, e.g. position 1, one cysteine and one mixture position; a tetramer having one predetermined position, one cysteine and two mixture positions; a 5-mer whose first position is defined (predetermined) and whose remaining positions are occupied by the required cysteine and mixtures at the other positions; a 5-mer whose first and fifth positions here defined residues, whose second position is cysteine, and whose third and fourth positions are occupied by mixtures; a 6-mer whose first position is predetermined, whose second is cysteine, and whose last four are occupied by mixtures; a hexamer whose first three positions are predetermined, whose fourth position is cysteine, and whose last two positions are occupied by mixtures; a 7-mer whose first position and positions 4–7 are mixtures and whose second position is cysteine, and third position is predetermined; a 7-mer whose first, third and fourth positions are predetermined, whose second position is cysteine and whose remaining positions are mixtures; an 8-mer whose third and fourth positions are predetermined, whose first position is cysteine, and whose remaining positions are occupied by mixtures of residues; an 8-mer whose first four positions are predetermined, whose C-terminal position is cysteine and whose three remaining positions are each mixtures; a 9-mer whose fourth and fifth positions are predetermined, whose first (N-terminal) position is cysteine, and whose remaining positions are mixtures; a 10-mer whose positions 3–7 are of a predetermined sequence, whose position 2 is cysteine and whose remaining positions are occupied by mixtures; a 10-mer whose first position is predetermined, whose C-terminus is cysteine, and whose remaining positions are occupied by mixtures; a 10-mer whose positions 7–9 are predetermined, whose first position is cysteine, and whose remaining positions are occupied by mixtures, and the like.

In another exemplary particularly preferred embodiment, each precursor oligopeptide portion comprises equimolar amounts of linear oligopeptide chains containing the same number of three to about ten amino acid residues in each chain. Such a precursor portion, and its members, have only one, single, predetermined amino acid residue e.g. Ala, D-Val, Ser, etc., at a singly predetermined position of the oligopeptide chain, e.g. positions 1, 2, 3 . . . 10 from the amino-terminus, the one required cysteine that forms part of the cystine bond between the two parts of the dimer molecule, and all of the remaining positions occupied by equimolar amounts of at least six different residues, with C- and N-termini as discussed before.

Thus, each of the exemplary precursor oligopeptide mixtures has equimolar amounts of the same at least six different amino acid residues at the positions other than that of cysteine and the single, predetermined amino acid residue present at the predetermined chain position, and that single residue is one of the same at least six different amino acid residues. Each of the plurality of mixtures differs from the other mixtures by the identity of the single, predetermined amino acid at the predetermined chain position.

As illustrative, a precursor second oligopeptide mixture portion has a cysteine at the same position in each chain and can have each remaining position of the oligopeptide chain occupied by an equimolar mixture of the same residues used in the first oligopeptide mixture. Preferably, at least one position in the chain of each oligopeptide of the mixture is occupied by the same, single amino acid residue. In other embodiments, up to all of the chain positions except those occupied by the cysteine and the one equimolar mixture position can be occupied by a single predetermined residue, as was discussed previously.

Thus, as to the number and position of single, predetermined residues present, the single cysteine residue and the position and number of mixture positions, a precursor second oligopeptide mixture can resemble a precursor first oligopeptide mixture. Indeed, the precursor first oligopeptide portions and second oligopeptide mixture portions and those mixtures in the dimer oligopeptide mixture set can be identical in every respect so that the dimeric molecules are homodimers. Such homodimeric oligopeptide mixture sets are one preferred embodiment of the present invention.

Where the precursor first oligopeptide portion and second oligopeptide mixture portions differ as to oligopeptide chain length, number or position of mixture positions, number or identity of predetermined amino acid residues, or position of the cysteine residue, the dimer molecules prepared are heterodimers.

Once the first precursor oligopeptide portions and second precursor oligopeptide mixture portions are prepared, the dimeric oligopeptide mixture sets can be prepared by a number of procedures. In one preferred embodiment, illustrated hereinafter, equimolar amounts of both precursor mixtures are admixed in an aqueous reaction mixture and gently oxidized as with hydrogen peroxide to form a disulfide bond-containing dimeric oligopeptide mixture set. The oxidation reaction is maintained until no further free mercaptan (—SH) group is detected as with Ellman's reagent.

It should be apparent that such dimeric molecule sets statistically contain about 50 percent heterodimers and 25 percent of each homodimer prepared by the self-reaction of each of the precursor oligopeptide portions. Such dimer mixtures are considered to be heterodimers because of the greater amount of those dimers present.

Homodimeric molecules that are substantially free of heterodimeric molecules can also be prepared by a similar oxidation of a single appropriate precursor oligopeptide mixture.

Homodimeric molecules can also be prepared by first reacting the mercaptan group present in each chain of a mixture with a disulfide-forming thiol (mercaptan) protecting group such as Ellman's reagent [5,5'-dithiobis(2-nitrobenzoic acid)] to form an unsymmetrical disulfide-containing oligopeptide mixture. The unsymmetrical disulfide-containing oligopeptide molecules of that mixture can then be reacted with an equimolar amount or slight excess of the mercaptan-containing form of the same oligopeptide mixture in an aqueous medium at about pH 6.8 in the presence of EDTA or similar sequestrant to form homodimeric molecules. Any unreacted molecules free of a disulfide bond between two oligopeptide chains can be removed by chromatographic techniques on the basis of molecular weight. A similar chromatographic technique can also be used with the simple oxidation approach, or any of the other synthetic procedures discussed herein.

A before-described mixed disulfide-containing oligopeptide mixture can also be utilized to form heterodimeric oligopeptide mixture sets that are substantially free of homodimer molecules, as well as free of other oligopeptide molecules that do not contain a cystine disulfide bond. Here, the mixed disulfide-containing oligopeptide mixture is reacted with a different precursor oligopeptide portion containing a free mercaptan group using the same reaction conditions noted before. A similar reaction, using sodium arsenite to stabilize adjacent thiols, was reported for joining two different Fab' groups in Brennan et al., *Science*, 229:81–83 (1993).

A homodimer such as prepared by mild oxidation of a single oligopeptide mixture can also provide the basis for synthesis of heterodimeric oligopeptide mixture sets that are substantially free of homodimer molecules or other peptide-containing molecules that do not contain a cystine disulfide bond. This process for heterodimer formation is similar to a process well known in the hair straightening arts for breaking and then remaking cystine disulfide bonds within hair fibers.

Here, the homodimer molecules are first reacted with an appropriate bisulfite salt such as sodium or potassium bisulfites in an aqueous medium at a pH value of about 6.5–7.0 to form the corresponding oligopeptide mixture cysteinyl thiosulfonate (Bunte salt) from one portion of the dimer and a precursor cysteine-containing oligopeptide mixture from the other portion of the dimer. Use of an excess of the bisulfite salt with reoxidation of the cysteine residues to form further homodimers that are then cleaved to form more Bunte salt and further cysteine-containing oligopeptide mixture for further recycling can lead to a near quantitative formation of the Bunte salt-containing precursor oligopeptide portion. The Bunte salt-containing oligopeptide mixture can be separated from any homodimer or cysteine-containing oligopeptide on the basis of size and/or charge difference by standard procedures. The Bunte salt can also be formed as discussed in Chen, *Biochemistry*, 7:4247–4254 (1968).

The Bunte salt-containing oligopeptide mixture is thereafter reacted in an aqueous reaction medium at about pH 9–10 with another mercaptan-containing oligopeptide mixture to form a disulfide bond-containing heterodimer oligopeptide mixture set. The thus formed heterodimer molecules can be separated from any unreacted Bunte salt- or mercaptan-containing oligopeptide mixtures on the basis of molecular weight and/or charge as before. It is preferred that each above reaction be run to completion to help assure that the various members of the mixture remain present. To that end, it is preferred that one of the two reacting oligopeptide mixtures be present in slight excess.

Regardless of which process is used for preparation of dimeric oligopeptide mixture sets, once prepared, the mixture sets are preferably recovered, and can be further purified or desalted if desired. After desalting by standard techniques such as by dialysis or ultrafiltration, where desired, a mixture set can be recovered by freeze drying. The dimeric oligopeptide mixture sets can also be used without recovery by use of aliquots of the reaction medium.

It is presently impossible to identify all of the oligopeptides in a mixture the complexity of some of those described herein such as those containing millions of different dimer molecules. However, by using the synthetic methods discussed before, a skilled worker can construct a precursor oligopeptide equimolar mixture, which upon hydrolysis and amino acid analysis has molar ratios of each mixture position amino acid to the others in the range of about 0.5 to about 1.5; i.e., the molar ratio of one amino acid residue to any other residue is 1:1± about 0.5, more preferably, this ratio is 1:1± about 0.25, which ratios carry through to the dimeric oligopeptide mixture sets.

Each chain of a dimer set is also present in an equimolar amount and is of the same length (contains the same number of residues) compared to the other chains present in the set. This equimolarity is also impossible to measure directly for many of the contemplated mixtures. However, by carrying out each reaction to completion and maintaining the previously discussed equimolarity, one can prepare chains that are of the same length and are present in equimolar amounts.

It can also be useful for a dimeric oligopeptide mixture set to include a label. A radioactive label such as $^3$H can be used as part of an N-terminal acyl group of each member oligopeptide.

Other contemplated labels include chromophores such as the 2,4-dinitrophenyl or 4-nitrophenyl groups and fluorescent molecules such as a dansyl group that can be coupled to an N-terminal amino group of a precursor oligopeptide using dansyl chloride (5-dimethylamino-1-naphthalenesulfonyl chloride).

A 2,4-dinitrophenyl or 4-nitrophenyl group can be coupled to an N-terminal amino group of a precursor oligopeptide by means of an appropriate halogen derivative such as a chloro or fluoro group. The resulting nitrophenyl aniline derivatives have a yellow to yellow/orange color that can be readily observed.

It is also contemplated that a photoreactive label be coupled to a dimeric oligopeptide mixture set, particularly at the N-terminus. Exemplary photoreactive labels include the 4-azidobenzoyl and 4-azidosalicyl groups that are present as N-terminal amides prepared by reaction of the N-hydroxysuccinimide ester of either group with the free, N-terminal oligopeptide amino group. Each of the esters is available from Sigma Chemical Co., St. Louis, Mo.

Libraries of Sets and Optimal Ligand Sequence Determination

As noted earlier, a contemplated dimeric oligopeptide mixture set is used as a ligand that binds to a receptor (or acceptor) such as an antibody combining site, an enzyme or other biological receptor such as an opiate receptor. To determine optimal binding to a receptor of choice, it is convenient to utilize a library of dimeric oligopeptide mixture sets in which each set is identical except for: (a) the position of the one or more predetermined amino acid residues in the oligopeptide chain; (b) the identity of the one or more predetermined residues; or (c) both the position and identity of the one or more predetermined amino acid residues. Libraries comprising dimer sets described herein are thus contemplated.

The above types of libraries (a), (b) and (c) can be further understood by way of example, using only a single trimer oligopeptide residue whose positions are occupied by individual residues or mixtures having the sequence ABD, and excluding the mercaptan-containing residue. Thus, where A is a predetermined residue $O_1$, one mixture set has the sequence $O_1BD$. A library where only the position of that predetermined residue differs, (a), includes sets $O_1BD$, $AO_1D$ and $ABO_1$. A library in which only the identity of a predetermined residue differs, (b), includes the sets $O_{1-a}BD$, $O_{1-b}BD$, $O_{1-b}BD$ ... etc. where the subscripted "1-a", "1-b", "1-c" etc. are different residues of the at least six. A library whose sets differ in both the position and identity of a predetermined residue includes sets $O_{1-a}BD$, $O_{1-b}BD$, $O_{1-c}BD$ etc. as well as $AO_{2-a}D$, $AO_{2-b}D$, $AO_{2-c}D$, etc.

It should be apparent that where only the position or both the position and identity of a predetermined residue(s) is different, a residue occupying a given position in one set is not present in a second set because the predetermined residue is at that position. A chain position occupied by an equimolar mixture of the at least six residues is usually and preferably the chain position at which the sets differ.

Libraries of sets that differ in both the position and identity of the predetermined residue can be illustrated using the above exemplary sequence ABD, where X is an equimolar mixture of residues. One library thus has the sequence $O_{1-a}XD$, $O_{1-b}XD$, $O_{1-c}XD$, etc., whereas another library has the sequence $XO_{2-1}D$, $XO_{2-b}D$, $XO_{2-c}D$, etc. Residue D can be a single residue or a mixture.

More specifically, in one embodiment, each member set of a contemplated library contains dimeric oligopeptides of the same length, having the same N- and C-termini, an oxidized mercaptan-containing residue at the same positions in each chain (although the position in one chain need not be the utilized in the other chain), one or more (at least one) predetermined amino acid residues at the same one or more predetermined positions in at least the chains of the first oligopeptide mixture, and each set has the same sequence of equimolar amounts of at least six different amino acid residues at one or more (at least one) predetermined positions of at least the chains of the second oligopeptide mixture portion. The sets within the library differ in that the at least one predetermined residue present at a predetermined chain position within each set is different between the sets; i.e., the sets differ in the identity of the one or more, preferably one, predetermined residues of the chain.

In one exemplary library of heterodimeric oligopeptide mixture sets, a first set comprises dimer molecules in which the first chain position of a first 4-mer oligopeptide portion is occupied by a predetermined amino acid residue such as alanine, the second position is occupied by the oxidized cysteine and each of the third and fourth positions is occupied by equimolar amounts of each of the naturally occurring L-amino acids except cysteine, whereas the second oligopeptide mixture of that dimer molecule is also a 4-mer that contains the oxidized cysteine at position 2 and positions 1, 3 and 4 are occupied by equimolar amounts of the same nineteen residues used in the first oligopeptide mixture portion.

The second set of this library is identical to the first set except that instead of an alanine residue at position 1 of the first oligopeptide portion, a valine is present. The remaining sets of this exemplary library differ from the first two sets in having a different one of the remaining seventeen naturally occurring amino acid residues at position 1 of the first oligopeptide chains. The sets of the above library thus differ in the identity of the one, single residue at a predetermined position of the oligopeptide chain.

Separately assaying each set with the receptor of choice in an aqueous medium for a given study provides the identity of the amino acid residue at position 1 of the first oligopeptide chain that exhibits optimal binding to that receptor. In some instances, two or more residues provide similarly optimal binding.

Upon determining which one or more residues at position 1 of the first oligopeptide mixture exhibited optimal binding, a second library of sets is assayed. In this library, position 1 of the first oligopeptide chain is occupied by the residue that exhibited optimal binding in the first library as discussed before, the second position is occupied by the oxidized cysteine, the third position is occupied by a predetermined single residue of the nineteen used as before, the fourth position is occupied by equimolar amounts of the same eighteen residues used at the mixture positions. The second oligopeptide portion is as before.

This second exemplary library also has nineteen sets as did the first library, and each of those nineteen sets is separately assayed to determine which residue(s) at position three provides optimal binding with the same receptor as used with the first library. Determination of the residue that exhibits optimal binding at position 3 provides the identity of the first three residues of the sequence of an optimal binding dimer molecule.

A third exemplary dimer library of cystine-linked 4-mers is prepared in which the residues at positions 1 and 3 are those previously determined to provide optimal binding, the oxidized Cys is at position 2, and one each of the above nineteen residues of the mixture positions occupies position 4 (the C-terminus) of the first oligopeptide portion. The second portion of this third dimeric oligopeptide mixture set is also as before discussed.

The third library is assayed as discussed before and a residue that exhibits optimal binding at position 4 is determined. Determination of that last residue completes the sequence of the first oligopeptide portion and provides a single, optimal binding sequence. Each member of the before-described third library contains one oligopeptide portion having a complete, predetermined sequence.

A fourth nineteen set library is thereafter constructed in which the complete 4-mer sequence determined above for the first oligopeptide portion is cystine-bonded to a second oligopeptide mixture portion that in one set has a predetermined one of the before-discussed amino acid residues such as alanine at position 1, the oxidized cysteine forming part of the cystine disulfide bond at position 2, and equimolar amounts of the same nineteen residues used before at positions 3 and 4 of the oligopeptide chains.

The remaining sets of this library each contain a different one of the remaining eighteen amino acid residues at position 1 of the second oligopeptide mixture portion, with the remainder of the molecules being otherwise identical to that of the set whose first four positions were determined. These sets are assayed as before to determine a residue that exhibits optimal binding and thereby define the residue at position one of the other portion of the dimer.

The before-described library assays are repeated for the next position in the sequence using another library of sets, and the set that exhibits optimal binding is determined, thereby defining an optimal binding residue for that specified position. Determination of an optimal binding residue at position 3 provides the sequence for all but one position in the dimer sequence. Nineteen individual peptide dimers are then synthesized and assayed to complete the sequence by determining the residue that exhibits optimal binding at the last position, and thereby the sequence of an oligopeptide dimer ligand that exhibits optimal binding to a chosen receptor.

Each of the above libraries also has sets that differ from each other by the identity of the one, single predetermined residue.

In another embodiment, the first and second oligopeptide portions of a first mixture set are the same so that the first library contains sets of homodimers. An exemplary library contains chains of four residues each in which the N-terminal residue has an acetyl group (Ac) and the C-terminal residue has an amide (—NH2) group. The second position of each chain in the library contains the oxidized cysteine that forms the cystine disulfide that bonds the two portions together. The first residue position in each chain is one of the 20 natural L-amino acids except cysteine, with the same residue being present in each chain. The oligopeptides of each molecule portion are mixtures having equimolar amounts of those same nineteen residues at each remaining position of the chain at both portions. Screening of these nineteen homodimer sets provides the identity of the first residue in each chain that exhibits optimal binding.

Further homo- or heterodimer libraries can thereafter be synthesized in which only one residue in both chains or one residue in each chain is changed in each iteration until an optimal binding sequence is determined using the iterative synthesis-assay procedure discussed before.

In yet another embodiment, nineteen precursor oligopeptide mixtures are prepared whose first position is occupied by one of the above nineteen naturally occurring amino acid residues other than a mercaptan-containing residue, e.g., cysteine, the second position is occupied by the required cysteine residue and the third and fourth positions are occupied by equimolar amounts of those same nineteen residues. Each of those nineteen mixtures is reacted with itself and with each of the remaining eighteen mixtures to form 190 dimer mixture sets (19+18+17+16+15+14+13+12+11+10+9+8+7+6+5+4+3+2+1=190) of which 19 are homodimers and the remainder are heterodimers.

Those 190 dimer mixture sets can also be viewed as nineteen oligopeptide dimer mixture libraries, some of whose member sets are redundant between libraries. Thus, each library contains one predetermined position in one chain that is constant, with one predetermined position in the other chain differing among the nineteen residues.

Screening those 190 sets using a binding assay as discussed before provides the identity of one residue at the first position of the oligopeptide mixture in each portion of the molecule that provided optimal binding.

With that knowledge in hand, nineteen further precursor mixtures are prepared in which the first position of each chain is occupied by the residue that provided optimal binding for that chain in the previous assay, the second position is occupied by the required cysteine used to form the cystine disulfide, nineteen individual residues occupy the third position and the fourth position is an equimolar amount of all nineteen residues. Another nineteen precursor mixtures are prepared having the residue that provided optimal binding for that portion of the molecule at position 1 and positions 2, 3 and 4 are occupied as discussed immediately above.

Those two groups of nineteen precursor mixtures are individually reacted with each other to form the dimer sets. Where the same or a similar (within a factor of about 2) optimal binding value is exhibited by the same residue at position 1 in both portions of the molecule (homodimer) as compared to dimers where those residues are different (heterodimer), both precursor mixtures utilize that same residue at position 1 so that the above further precursor mixture is redundant of the first-named precursor mixture and each mixture of that first-named precursor mixture is reacted individually with itself and the other eighteen members to form 190 dimer mixture sets. If the determined optimal binding value for a heterodimer whose first position residue of one chain is different from the first position residue of the other chain is about a factor of two or more better than that observed where the first position residues in both chains are the same, the before-mentioned further precursor mixture is generally utilized in preparing the next dimers and that number of dimeric oligopeptide mixture sets that is prepared from the two precursors is 361 (19×19).

Assaying of the produced dimers as discussed before provides the identity of the position 3 residue in each of the chains.

The above process identifies residues two at a time, one in each portion of the dimer molecule. It should be understood that after the two first position residues are identified, one portion of a dimer molecule can be held constant while optimal binding residues in the other portion are identified. Determination of optimal binding ligand sequences can also proceed by identifying non-adjacent residues, although the identification of adjacent residues is preferred.

A before-discussed process can be generally described to comprise the steps of:

(a) Providing a library of dimeric oligopeptide sets as discussed generally before, except that here, each set in the library differs from the other sets in the identity of the one or more predetermined amino acid residues in the oligopeptide chain.

(b) Each set from the library of sets is separately admixed with the acceptor in an aqueous medium at a set concentration of about 0.1 milligrams per liter to about 100 grams per liter. The binding of each set to the acceptor is separately assayed, and a set exhibiting preferential binding relative to the other sets is determined, thereby identifying an amino acid residue that provided preferential binding at the one or more predetermined positions.

(c) A second library of sets is provided that is identical to the first library except that each oligopeptide chain has (i) the amino acid residue identified in step (b) at the one or more predetermined positions and (ii) a predetermined one of the at least six different amino acid residues at another predetermined position of the oligopeptide chain that is different from the one or more positions of the identified amino acid residue of the first-named library of sets. The second library of sets has equimolar amounts of each of the at least six different amino acid residues of the first-named sets at the same one or more positions of the dimeric oligopeptide chains not occupied by the (i) identified amino acid residue(s) or (ii) predetermined amino acid residue(s).

(d) Each set of the second library of sets is separately assayed with the acceptor in an aqueous medium at a set concentration of about 0.1 milligrams per liter to about 100 grams per liter. The binding of each set to the acceptor is separately assayed, and a second set exhibiting preferential binding is determined, thereby identifying an amino acid residue that provides preferential binding at the other predetermined position in the oligopeptide chain.

(e) Steps (c) and (d) are repeated using zero through fifteen further libraries of sets of dimeric oligopeptide mixture sets instead of the second library of sets or until preferential binding does not increase when a further library is assayed. Thus, the above-recited steps through step (d) define three positions of a sequence including the mercaptan-containing residue, and are used where the first library contained a first oligopeptide portion that is completely defined and a second oligopeptide mixture portion containing one defined chain position, the mercaptan-containing residue and one mixture position. Further iterations are therefore not used.

Strictly speaking, the "library" of steps (c) and (d) is not a "library" as that term has been previously defined because there is no mixture position and each of the dimer oligopeptides is in fact a single dimer. However, for convenience in description, those dimer oligopeptides are considered to be a "library". Steps (f) and (g) discussed hereinafter define those cases for other than zero repeats of steps (c) and (d).

Where the libraries contain oligopeptide portions each of which contains 10 residues, eighteen positions are undefined. Steps of the above process through step (d) bring the undefined positions to sixteen. Once all but the last positions are defined, individual dimer molecules are utilized in the process as is discussed below, so for a dimer oligopeptide whose two portions each contain 10 residues, a total of fifteen iterations (repeats) of steps (c) and (d) can be used.

Each step (e) further library of sets of dimeric oligopeptide mixture sets comprises a mixture of equimolar amounts of member dimeric oligopeptide chains containing the same number of amino acid residues in each dimeric oligopeptide chain as the chains of the first-named library of sets. The member chains of the sets of each further library contain the amino acid residues in the dimeric oligopeptide chain positions that exhibited preferential binding in a library of sets used immediately before, and a predetermined one of the at least six different amino acid residues at another predetermined position of the dimeric oligopeptide chain different from the positions of the identified amino acid residues of the library of sets used immediately before. Each of the further library of sets has equimolar amounts of the at least six different amino acid residues of the first-named sets at the same one or more positions of the oligopeptide chain not occupied by the identified amino acid residues or the predetermined amino acid residues.

(f) Where one position of the dimeric oligopeptide chain that provides preferential binding is not identified, at least six dimeric oligopeptide chains are provided in which each chain contains the same number of amino acid residues in each dimeric oligopeptide chain as the chains of the first-named plurality of sets. Each dimeric oligopeptide chain contains the identified amino acid residues in the oligopeptide chain positions that exhibited increased preferential binding in the immediately preceding assay of step (e) and a predetermined one of the at least six different amino acid residues at another predetermined position in the dimeric oligopeptide chain different from the positions of the identified amino acid residues used in the immediately preceding assay of step (e).

(g) Each of the at least six dimeric oligopeptides of step (f) is separately admixed with the acceptor in an aqueous medium at a dimeric oligopeptide concentration of about 0.1 milligrams to about 100 grams per liter, is separately assayed for the binding of each dimeric oligopeptide, and the dimeric oligopeptide that exhibits preferential binding is determined, thereby determining the sequence of a dimeric oligopeptide ligand that preferentially binds to the acceptor.

It sometimes occurs that no binding preference is observed at a particular position along a chain. Where that is the case within a chain, any convenient amino acid residue is used to define that position. Where that condition continues through the remainder of a given sequence, the acceptor (receptor) binding pocket may be filled by the defined positions and convenient residues are again utilized for the remainder of the positions. This phenomenon typically indicates that the chain length of the oligopeptide portion whose sequence is being changed can be shortened to exclude those "convenient" residues and simplify syntheses.

Each of the above libraries of dimer sets prepared after the first library was prepared was synthesized knowing which residue at an exemplary position exhibited optimal binding. Thus, knowledge gained from the first library was used in synthesizing the second having an adjacent predetermined residue, and so on. That iterative synthesis-assay-adjacent-synthesis technique can be particularly useful. It is preferred, but not required, that adjacent optimal binding residues be determined seriatim. Non-adjacent optimal binding residues can also be identified at each iteration.

In another embodiment, knowledge gained from initial assays is not used in the synthesis of libraries. Rather, libraries that differ in both the position and identity of the predetermined residue are used.

In this embodiment, exemplary precursor oligopeptide mixtures are prepared that contain one each of the at least six, and more preferably at least 10, and most preferably, about 15 to about 20 residues such as the nineteen residues used before as exemplary at a known position in the chain, a mercaptan-containing residue (e.g., cysteine) at another position and equimolar amounts of the same nineteen residues at the other chain positions to be examined for binding.

Taking a heptamer precursor in which each chain has an N-terminal acetyl group and a C-terminal amide as exemplary, nineteen precursor mixtures are prepared having chains whose first position is occupied by a single one of the before-discussed nineteen residues, positions 2, 3, 5, 6 and 7 are occupied by equimolar mixtures and whose position 4 is occupied by cysteine. Another group of nineteen precursor mixtures is prepared whose second position is occupied by a different single one of those nineteen residues, whose positions, 1, 3, 5, 6 and 7 are equimolar mixtures of the nineteen residues, and whose position 4 is occupied by cysteine. A third group of nineteen oligopeptide mixtures is prepared having a different single one of the nineteen residues at position 3, equimolar mixtures of residues at positions 1, 2, 5, 6 and 7 and the cysteine at position 4. Three further groups of nineteen precursor oligopeptide mixtures are prepared, each precursor mixture having the cysteine at position 4, a different single residue of the nineteen at positions 5 (group four), 6 (group five) and 7 (group six), and equimolar amounts of the nineteen residues at the remaining positions.

Each group of nineteen precursor oligopeptide mixtures is separately reacted with itself and with the other members of its group to form 190 dimer oligopeptide mixture sets per group, defining 19 libraries per group as discussed before. The six groups together thus constitute 1140 (6×190) dimer oligopeptide mixture sets.

The above 1140 dimer oligopeptide mixture sets also define libraries of sets in which the identity of the one, single predetermined residue is the same, but the position of that predetermined residue is different. For example, there are nineteen homodimers at each position. Those homodimers define six libraries of nineteen sets each whose predetermined residues are the same, but whose position in the chain differs, with each position of difference being occupied by an equimolar mixture of residues when not occupied by a predetermined residue. There are similar libraries for each of the heterodimer mixtures present.

Taken together as a group, those 1140 dimer oligopeptide mixture sets define a library in which both the position and identity of the one or more predetermined amino acid residues differ from each other.

Each set of dimer molecules is assayed for optimal binding with a receptor (acceptor) of choice. The results of optimal binding studies within each group of 190 dimer sets provide the identities of two residues at a time, one in each chain, that exhibit optimal binding to the chosen receptor. The results obtained for each chain position from all of the groups provides a sequence for an optimal binding sequence.

In an alternative embodiment, each of the above six groups of nineteen precursor oligopeptide mixtures (6×19=114 mixtures in all) as a precursor first portion is reacted with a second oligopeptide mixture portion having a cysteine at position 4 and all other positions of difference occupied by equimolar mixtures of the nineteen residues to prepare 114 (6×19×1=114) heterodimer oligopeptide mixture sets. Those sets are assayed for optimal binding, with the optimal binding residue at each chain position defining a complete optimal ligand sequence for a first portion of the molecule.

The above 114 dimer sets also define libraries where sets differ as to the identity of the predetermined residue, libraries whose sets differ in the position of the predetermined residue, and as a whole, define a library whose sets differ both as to identity and position of the predetermined residue.

A single oligopeptide precursor having the above-defined sequence is prepared as a precursor second oligopeptide portion and that single sequence is reacted with each of the above 114 first oligopeptide precursors to form another 114 (1×19×6) dimer oligopeptide mixture sets. Similar receptor binding studies are again carried out with the residue exhibiting optimal binding at each position defining the sequence for the second portion of the ligand, and thereby the entire ligand.

The use of dimer sets having chains with a single one of at least six residues at one position and equimolar mixtures of those at least six residues at the other positions along with the required cystine disulfide link is referred to as "positional scanning" in that optimal binding for each chain position is separately assessed without reference to a prior result.

An above process can be carried out using two libraries. The sets of one library contain at least one chain position that is occupied by an equimolar mixture, and another whose residues are scanned. The second library has sets in which the position in the first library that was occupied by the equimolar mixture is occupied by individual residues that are scanned, and in which the position in the first library that was scanned is occupied by an equimolar mixture. It is preferred, however, that a plurality of positions such as at least four positions be scanned so that at least four positions in both chains are alternatively scanned or occupied by equimolar mixtures of residues in given libraries. It should be apparent that one or more positions in a dimer molecule can be occupied by the same one or sequence of residues with the other positions being scanned or occupied by equimolar mixtures.

A generalized positional scanning process for determining the sequence of a dimeric oligopeptide that preferentially binds to an acceptor comprises the steps of:

(a) providing a library of oligopeptide mixture sets as discussed generally before in which each set of this library differs from the other sets in the identity and chain position of a single predetermined amino acid residue of the at least six different residues at the predetermined position within the set, and in which each chain position of difference is occupied by an equimolar mixture of at least six different residues when it is not occupied by a predetermined residue.

(b) Each set is separately admixed with the acceptor in an aqueous medium at a set concentration of about 0.2 milligrams per liter to about 100 grams per liter, and the binding of each set to the acceptor is separately assayed.

The amino acid residue that exhibited preferential binding at each position of the oligopeptide chain of each set that differs from the other sets provides the sequence of a dimeric oligopeptide that preferentially binds to the acceptor.

As was the case with the previously discussed procedures for determining the sequence of an optimal binding ligand, more than a single residue can exhibit similar optimal binding. It is also known that some receptors exhibit no preference for one residue over another at a particular sequence position, this latter phenomenon is referred to as positional redundancy.

In view of the often observed similarities exhibited by different residues at the same position and positional redundancy, any before described process for determining an optimal binding ligand sequences may not provide the sequence of a single oligopeptide ligand whose binding is the best of all of the millions of possible candidate ligand sequences. Nevertheless, an above process can narrow the number of candidates from millions to tens, hundreds or sometimes related thousands that are typically similar and can be readily prepared by usual techniques such as the SMPS procedure of U.S. Pat. No. 4,631,211.

Assays

A dimeric oligopeptide mixture set and its individual members can be looked at as donor (ligand) in donor-acceptor (receptor) binding complex formation. Exemplary acceptor (receptor) molecules are antibody combining site-containing molecules such as whole antibodies, F(ab), $F(ab')_2$ and Fv antibody portions, solubilized or non-solubilized cell surface receptor molecules, such as the solubilized CD4 receptor, internal cellular receptors, enzymes and viral protein receptors, all but the antibody combining site-containing molecules being collectively referred to as "cellular receptors". "Cellular receptors" also include living cells that contain receptors that interact with a dimeric oligopeptide library as ligand (donor).

Any well known binding or binding inhibition assay format can be used. Thus, homogeneous solution assays such as competitive enzyme inhibition assays, and heterogeneous assays such as solid phase assays and those utilizing whole cells are contemplated.

For example, a solid phase assay using a solid phase-bound antibody binding site-containing molecule such as a whole antibody and a radiolabeled dimeric oligopeptide mixture set is contemplated. Also contemplated is a competitive binding assay in which a protein or polypeptide is bound to a solid phase as an antigen and a monoclonal antibody or antibody combining site-containing portion binding to that antigen is admixed with a dimeric oligopeptide mixture set. Inhibition of binding of the monoclonal antibody by the dimeric oligopeptide mixture set provides a measure of the binding between the dimeric oligopeptides and monoclonal antibody. Monoclonal antibody binding inhibition and the inhibition of other acceptors' binding can be assayed using enzyme or radiolabels as is well known.

It is often the case that one has receptors (acceptors) such as antibodies to a particular ligand such as an antigen, but the specific ligand (antigen) that binds those antibodies is unknown. Under these circumstances, usual solid phase assays in which the ligand is affixed to a plate or other solid phase matrix cannot be carried out because the relatively short dimeric oligopeptide mixture sets contemplated herein do not bind as well to microtiter plate walls and similar solid phase matrices as do larger proteins.

Avidin binds well to microtiter plate walls and similar matrices. Use of that fact and its well known binding partner, biotin, can be made for those assays in which the ligand bond by the receptor is unknown or is otherwise unavailable.

Thus, avidin is coated on a solid phase matrix such as microtiter plate walls using standard, well known techniques such as adsorption. Biotin, which contains a free carboxyl group, is coupled to the N-terminal amines of each oligopeptide chain of a before-described dimeric oligopeptide mixture set via the biotin carboxyl group, using usual coupling chemistry as described herein for coupling amino acids. That coupling is preferably carried out just prior to cleavage of precursor molecules from their solid supports. The biotinylated dimer set is dissolved in an aqueous medium and admixed with the avidin-coated solid phase matrix to form a solid/liquid phase admixture. That admixture is maintained for a time period sufficient for the avidin and biotinylated dimeric oligopeptide mixture set to complex, typically five minutes to about five hours, and form a biotinylated dimeric oligopeptide mixture set-containing solid support and a liquid phase depleted of biotinylated dimeric oligopeptide. The solid and liquid phases are then separated, and the solid support is typically washed.

The thus prepared solid support that contains an affixed dimeric oligopeptide mixture set, is then utilized with the receptor (acceptor) in standard solid phase assays. Where the receptor is an antibody, usual detecting systems such as the use of radiolabeled or enzyme-linked anti-antibodies such as goat anti-mouse antibodies where the receptors are mouse antibodies are utilized to detect binding. Where the receptor is a cellular receptor, radiolabels incorporated into the receptor by culture of the cells in a medium containing radioactive amino acids are typical detecting means of choice.

It is frequently convenient to provide a spacer group between the dimeric oligopeptides of a set and the biotin. Exemplary spacers include one to about five glycine residues, or generally, $C_2$–$C_6$ straight chain ω-amino acids such as glycine, α-alanine, 4-aminobutyric acid (GABA) or 4-aminocaproic acid.

Thus, a N-terminal biotinylated dimeric oligopeptide mixture set as otherwise described before is also contemplated. That biotinylated dimeric oligopeptide mixture set can further include one to about five $C_2$–$C_6$ straight chain ω-amino acid residues between the N-terminal amine of the dimeric oligopeptides and the biotin group.

For a chromophore- or fluorescent-labeled dimeric oligopeptide mixture set, contact between the acceptor and dimeric oligopeptide mixture set can be carried out with the acceptor linked to a solid support such as sepharose or agarose. The non-binding and poorer binding dimeric sets can be separated from the solid support-bound acceptor molecules by washing at increasingly higher salt concentrations until a predetermined concentration is reached that is used to define a better or preferential or optimal binding dimeric oligopeptide mixture set. The choromophoric or fluorescent label can be used to follow the elution. Using the 2,4-dinitrophenyl chromophore as exemplary, the presence of a yellow to yellow/orange color on the solid support for a given set after washing indicates an optimal binding set.

An exemplary assay using a photoreactive label can be carried out with an enzyme having a known substrate. Here, the enzyme as acceptor (receptor) and photoreactive labeled, dimeric oligopeptide mixture set are admixed and the admixture maintained so that binding can occur. The admixture is then irradiated using sufficient quanta of light at an appropriate wavelength, as are well known, to cause the decomposition of the photoreactive group such as an azide group and the insertion of the resulting dimeric oligopeptide-containing radicals into the enzyme polypeptide backbone. That insertion links the dimeric oligopeptides of the set to the enzyme and blocks reaction with the enzyme's substrate. Thus, an assay of enzymic activity after irradiation provides a determination of which dimeric oligopeptide mixture set bound optimally, with a diminished enzyme activity indicating enhanced binding.

Cellular receptor molecules are also particularly contemplated as useful in this assay system. The cellular receptor whose binding is contemplated for assay need not be isolated, but can be part of an intact, living cell or organism such as bacterial, yeast, fungal, mammalian or plant cells, or viruses. When such intact, living cells or organisms are utilized, relative binding amounts can be determined by the growth or inhibition of growth of the admixed, assayed cells or organisms. The aqueous medium here is a growth or culture medium, known to promote growth of the assayed cells or organisms.

The aqueous medium used in a binding assay can be extremely varied and includes tap water, distilled or deionized water, as well as a buffer solution as is used for antibody binding studies or a cell growth medium as is useful for culturing bacteria, yeast, fungi, plant or animal cells, all of which are well known to skilled workers.

The concentration of free acceptor molecules, including those obtained from cell preparations or those present in intact, living cells used for such binding assays is an assay-effective amount such as is normally used for such assays, and is well known in the art. It is to be understood that different concentrations of free acceptor molecules or those present in intact, living cells can vary with each acceptor studied.

The assay-effective amount concentration of a dimeric oligopeptide mixture set in a binding assay aqueous medium is typically selected so that the dimeric oligopeptide mixture set is present at concentrations of about 0.1 milligrams per liter to about 100 grams per liter and preferably about 1.0 μg/ml to about 100 mg/ml. Thus, when each oligopeptide mixture is made up of about 2.5 million individual oligopeptide dimers; e.g. a dimeric 4-mer one of whose portions has one defined position, a cysteine and two mixture positions linked to a second portion having three mixture positions using 19 of the 20 natural amino acid residues, then each 8-mer dimeric oligopeptide within each mixture is present in a preferred concentration of about 1.0 μg/ml/2,500,000=0.4 pg/ml, to about 100 mg/ml/2,500,000=40 ng/ml. Presuming an average molecular weight of a dimeric 4-mer (eight total residues) N-acetyl C-amido oligopeptide to be about 920 g/mole, then at 1.0 μg/ml, the individual dimers are present at a concentration of about 0.4 pmolar and at 100 mg/ml the individual dimers are present at about 40 nmolar. More preferably, concentrations of about 0.5 mg/ml to about 10 mg/ml are used.

It is to be understood that the wide breadth of concentrations specified above is intended to take into account the contemplated range of dimeric oligopeptide mixture sets that can have up to seventeen positions as mixtures and the fact that wide ranges of concentrations are often used for determining $IC_{50}$ and $K_j$ values.

A before-described assay can be carried out in vitro as well as being carried out in vivo. For in vivo assays, living plants such as tobacco, alfalfa, corn (maize), zinnias and the like are contemplated hosts, whereas small laboratory mammals such as rats, mice, guinea pigs, rabbits and dogs are contemplated hosts for animal assays.

A dimeric oligopeptide mixture set-containing composition can be administered and dimeric oligopeptides contacted with the acceptors internally or externally in plants through watering, misting of foliage, or injection. For the animals, a composition can be administered internally, orally or by injection such as intraperitoneally, subcutaneously or intramuscularly or topically as by application to skin for the contact between donor and acceptor to take place.

Binding here can be assessed by relative growth rate (positive or negative) or by the affect of the composition on one or more tissues, as through microscopic examination, by body temperature where pathogen-infected animals are used, and the like as are well known.

The following examples are intended to illustrate, but not limit, the invention.

EXAMPLE 1

Dimeric Oligopeptide Mixture Set Preparation

Two groups of nineteen tetrapeptide precursor oligopeptide mixtures were prepared using the physical mixture method of Houghten et al., *Nature,* 354:84–86 (1991). Both groups of precursor oligopeptide mixtures had an N-terminal acetyl group (Ac—) and a C-terminal amide group (—NH$_2$). The first group of nineteen oligopeptide mixtures had each one of the nineteen natural L-amino acid residues except Cys at position 1, a cysteine at position 2, and equimolar amounts of those nineteen residues at each of positions 3 and 4. The second group of nineteen oligopeptide mixtures had a cysteine residue at position 1, one each of the nineteen natural amino acid residues at position 2 and equimolar amounts of those nineteen residues at each of positions 3 and 4.

Each of the 38 oligopeptide mixtures so prepared was lyophilized after its preparation and reconstituted in 0.1 M HCl (10 percent to total volume) and water to a concentration of 5 mg/ml, and the resulting solution maintained on ice. These conditions retard air oxidation of the cysteine residues, and each precursor was checked to assure that no cysteine oxidation had occurred prior to the oxidation coupling discussed below.

Each of the nineteen precursors in each of the two groups was reacted with itself and with each of the other members of its group to form two groups of 190 dimeric oligopeptide mixture sets (two groups of libraries). The 190 dimeric oligopeptide mixture sets of the above first group of precursors having a cysteine at position 2 of the chains are referred to as Set 1, whereas the 190 dimeric oligopeptide mixture sets of the above second group of precursors having the N-terminal cysteine are referred to as Set 2.

The individual oxidations were carried out by adding hydrogen peroxide (H$_2$O$_2$) in a 5 molar excess over the two oligopeptide mixtures in 0.1 M NH$_4$HCO$_3$. The reaction was maintained for 15 minutes with gentle shaking. This oxidation procedure not only forms the disulfide bond, but also oxidizes methionines to methionine sulfoxide residues. A sample was then removed and checked for complete reaction using Ellman's reagent. If the reaction was incomplete, which rarely occurred, it was maintained for a further time period of five minutes or until no free mercaptan was present. When the assay with Ellman's reagent showed no unreacted mercaptan, the individual dimeric oligopeptide mixture sets were frozen immediately. The frozen mixtures were lyophilized twice and reconstituted in water for use in binding assays. Each of the two libraries contained about 24,760,990 (190×19$^4$) individual oligopeptides.

EXAMPLE 2

Binding Assay with Monoclonal Antibody 17D09

Each of the dimeric oligopeptide mixture sets of Set 1 was assayed for its ability to bind to monoclonal antibody 17D09. That monoclonal antibody binds to residues 101–106 of the hemagglutinin protein of the influenza virus. Pinilla et al., *Mol. Immunol.,* 30(6):577–585 (1993). Residues 101–106 of the flu hemagglutinin define a linear epitope free of basic residues.

Optimal binding was found when the first residues of each oligopeptide portion was lysine, IC$_{50}$=34 μM. Interestingly, each of the next sixteen best binding sequences of the 190 sets also had a lysine residue at position 1 of one chain.

Nineteen further precursor oligopeptides are being prepared having a lysine at position 1, a cysteine at position 2, one each of the nineteen residues at position 3 and equimolar amounts of the nineteen residues at position 4. Another 190 dimer oligopeptide sets will be prepared by self-reaction of those precursors,and their binding to monoclonal antibody 17D09 will be assayed to determine two further optimal residues. Those results will then be used to prepare still further dimer molecules to complete the sequence determination.

A parallel study will be conducted in which each of those nineteen precursors is reacted with a second precursor having lysine at position 1, cysteine at position 2 and equimolar mixtures of nineteen residues at positions 3 and 4. Remaining optimal Briefly, monoclonal antibody (mAb) 17D09 binds to the antigenic oligopeptide Ac-TyrProTyrAspValProAspTyrAlaSerLeuArg Ser-$NH_2$ (SEQ ID NO:2)

(Wilson et al., *cell,* 37:767–778 (1984). The oligopeptide of SEQ ID NO:2 was adsorbed to microtiter plates at 100 pm/well. After blocking non-specific binding positions, 25 $\mu$l of each dimeric oligopeptide mixture set (6 mM) was added to each well, followed by the addition of 25 $\mu$l of mAb 17DO9 at predetermined dilutions. Percent inhibition of antibody binding by each dimeric oligopeptide mixture set was determined relative to the 100 percent binding of the mAb to the antigenic peptide on the plate. The concentration of dimeric oligopeptide mixture set necessary to inhibit 50 percent antibody binding ($IC_{50}$) was determined by serially diluting the dimeric mixture sets prior to addition of the mAb.

EXAMPLE 3

Binding Assay with Monoclonal Antibody HyHEL-5

Monoclonal antibody HyHEL-5 was raised against hen egg white lysozyme and is known to recognize a discontinuous antigenic determinant of that protein. Sheriff et al., *Proc. Natl. Acad. Sci., USA,* 84:8075–8079 (1987). This monoclonal was a kind gift of Dr. Sandra J. Smith-Gill, a co-author of the above paper, of the Laboratory of Genetics, National Cancer Institute, Bethesda, Md. 20892.

Initial screening as discussed in Example 2 using Sets 1 and 2 of Example 1 indicated that dimer mixture sets having phenylalanine or tryptophan at the single defined position provided optimal binding.

Initial screening as discussed in Example 2 using Sets 1 and 2 of Example 1 indicated that dimer mixture sets having phenylalanine or tryptophan at the single defined position provided optimal binding. Neither residue is present in the native epitope of lysozyme.

Further studies are being carried out using precursor mixtures having a tryptophan at position 1, cysteine at position 2, each of the nineteen residues discussed before at position 3 and an equimolar mixture of those nineteen residues at position 4. Those precursors will be coupled with second precursor mixtures having a tryptophan at position 1, cysteine at position 2 and equimolar mixtures at positions 3 and 4 for the next iteration and optimal binding studies. An optimal binding sequence will be determined for the remainder of the dimer as discussed previously.

EXAMPLE 4

Trypsin Inhibitors

Dimeric oligopeptide mixture sets 1 and 2 were screened for binding to the enzyme trypsin by determining the ability of individual dimeric-oligopeptide mixture sets to bind to the enzyme and competitively inhibit the tryptic hydrolysis of $N^\alpha$-benzoyl-D,L-arginine-p-nitroanilide. of those 380 sets, the only set that exhibited inhibitory activity was a homodimer having methionine sulfoxide at position 1, oxidized cysteine at position 2 and equimolar mixtures of the nineteen residues at positions 3 and 4, a homodimer of Set 1. The inhibition observed was 55 percent at 5 mg/ml.

A second group of nineteen precursor oligopeptide mixtures was prepared having methionine at position 1, cysteine at position 2, nineteen individual residues at position 3 and equimolar mixtures of the nineteen residues at position 4. Each member of the precursor mixtures was individually reacted with itself and the other members of the group to form another 190 dimeric oligopeptide mixture sets.

Of those 190 dimer mixture sets, 27 that exhibited optimal binding provided between about 40 and about 80 percent inhibition at a concentration of 5 mg/ml. Each of those 27 dimer sets had lysine, tryptophan or arginine at chain position 3 of one portion of the dimer. In addition, of those 27 dimer mixture sets, seven dimer sets exhibited inhibitions of about 68–78 percent and four of those seven dimer sets had a tryptophan at the third position of one chain and a fifth had a tryptophan at both third positions (the homodimer). Lysine was present at the third position of at least one chain in the remaining two dimer set sequences. Tryptophan and lysine were thereby determined to be appropriate single residues for chain position 3 of both portions of the dimer.

Four groups of precursor oligopeptide mixtures and defined oligopeptide precursors were then prepared. Each group contained a methionine at position 1 and a cysteine at position 2. Two groups (A) had lysine at position 3 and two groups (B) had tryptophan at position 3 so that the N-terminal three positions were specifically defined for all four groups of precursors.

The fourth (C-terminal) position for one of the A groups was occupied by each of the nineteen residues (group A-1) so that group A-1 contained nineteen individual oligopeptide sequences. The fourth position for the second A group (group A-2) was occupied by equimolar amounts of the nineteen residues so that that group constituted a precursor mixture. The fourth positions of the two B group materials were similarly prepared to provide groups B-1 and B-2, respectively.

The four precursor groups so prepared were paired and reacted together to form four libraries of dimer oligopeptide mixture sets following the procedure of Example 1. Those pairings were as follows: A-1+A-2; B-1+A-2; A-1+B-2; and B-1+B-2. Each library contained 19 sets, each set having nineteen member oligopeptide chains present in equimolar amounts.

Those four libraries were then assayed as before. The mixture in which one precursor had the sequence Ac-Xaa-Cys-Trp-Arg-NH$_2$ (SEQ ID NO: 3; in which Xaa is methionine sulfoxide) and the other precursor was group A-2 or B-2 provided IC$_{50}$ values of 101 and 83 $\mu$M, respectively, with all other sets having IC$_{50}$ values greater than 200 $\mu$M.

The final residue of the ligand sequence was determined by separately reacting precursor oligopeptide SEQ ID NO:3 with each of the nineteen individual members of groups A-1 and B-1, thereby forming 38 individual dimeric oligopeptide ligands. Each of those individual dimers was assayed as before. Interestingly, only the homodimer,

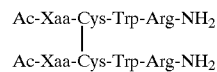

(SEQ ID NO:4; in which each Xaa is methionine sulfoxide) exhibited significantly enhanced inhibition over the IC$_{50}$=83 $\mu$M of the prior iteration. That value was 53 $\mu$M. Each of the next three optimal binding dimer molecules also contained SEQ ID NO:3 linked to a group A-1 sequence having a tyrosine (82 $\mu$M) or isoleucine (86 $\mu$M) residue at position 4 or a group B-1 sequence having a leucine at position 4.

The originally determined 55 percent inhibition at 5 mg/ml observed for the first dimeric oligopeptide mixture set is approximately an IC$_{50}$ value. therefore binding over that first, optimal binding dimer oligopeptide mixture set.

For these assays, 50 $\mu$l of dimeric oligopeptide mixture set solutions in water (0.5–5 mM) were added to 0.1 M Tris-HCl containing 0.025 M CaCl$_2$, pH 7.8 (100 $\mu$l), to which were added 15 $\mu$l of trypsin (bovine pancreas trypsin, Type I; Sigma Chemicals T 8003; 0.05 mg/ml in 0.02 N HCl ). The solution was maintained for 30 minutes, and the above substrate ($N^\alpha$-benzoyl-D,L-arginine-p-nitroanitide) was added (100 $\mu$l, 1 mg/ml in water). Absorbances at 405 nm were read using a Titertek multichannel photometer after another 30 minutes had elapsed and were expressed as a percentage of the control (absorbance of a solution without peptide).

EXAMPLE 5

Binding to Opioid Receptors

The enkephalins; i.e., TyrGlyGlyPheMet (YGGFM; SEQ ID NO:5) and TyrGlyGlyPheLeu (YGGFL; SEQ ID NO:6) were the first natural ligands found for the opioid receptors. These bind to three known receptor subclasses (mu, delta and kappa) with differing affinities [reviewed in Schiller, *Progress in Medicinal Chemistry*, Ellis et al. eds., Elsevier Science Publishers, U.K. (1990) pages 301–340]. The studies herein utilized an analog of met-enkephalin, [$^3$H]-[D-Ala$^2$, MePhe$^{4,}$Gly-O1$^5$]enkephalin (DAGO) that is known to bind specifically to the mu receptor using competitive binding studies with the dimeric oligopeptide mixture Sets 1 and 2 with rat brain homogenates containing mu specific receptors for opioid ligands.

The dimer mixtures that exhibited optimal binding were those of Set 1, and three of the four best binding dimer mixture sets contained an arginine residue at the first position of the sequence.

The best binding set of those dimer mixtures also contained a tryptophan residue at the first position of the other portion. That dimeric oligopeptide mixture set exhibited an $IC_{50}$ value of about 8.2 μM, which was almost one-half of the next three optimal binding dimeric oligopeptide mixture sets that exhibited $IC_{50}$ values of about 14.7, 14.9 and 18.4 μM, respectively. The before-described iterative process to define the remaining sequence positions based upon this first screening is underway.

The above assays were carried out using opioid receptors from rat brains prepared as follows. Particulate membranes were prepared using a modification of the method described by Pasternak et al., *Mol. Pharm.*, 11:340–351 (1975). Rat brains frozen in liquid nitrogen were obtained from Rockland Inc. (Gilbertsville, Pa.). The brains were thawed, the cerebella were removed, and the remaining tissue was weighed. Each brain was individually homogenized in 40 ml Tris-HCl buffer (50 mM, pH 7.4, 4° C. ) and centrifuged (Sorvall RC5C SA-600 16000 rpm) for ten minutes. The pellets were resuspended in fresh Tris-HCl buffer and incubated at 37° C. for 40 minutes. Following incubation, the suspensions were centrifuged as before, the resulting pellets were resuspended in 100 volumes of Tris-HCl buffer, and the suspensions combined. Membrane suspensions were prepared and used in the same day. Protein content of the crude homogenates ranged from 0.15–0.2 mg/ml as determined using the method described by Bradford, *Anal. Biochem.*, 72:248–254 (1976).

Binding assays were carried out in polypropylene tubes. Each tube contained 0.5 ml of membrane suspension, 8 nM of $[^{3}H]$-$[D$-$Ala^{2}$,MePhe$^{4}$·Gly-Ol$^{5}$]enkephalin (DAGO) (specific activity=36 Ci/mmole, 160,000 cpm/tube; obtained from Multiple Peptide Systems, Inc., San Diego, Calif. through NIDA drug distribution program 271–90–7302), 10 mg/ml of dimer oligopeptide mixture set and Tris-HCl buffer in a total volume of 0.65 ml. Assay tubes were incubated for 60 minutes at 25° C. The reaction was terminated by filtration through GF-B filters on a Tomtec harvester (orange, Conn.). The filters were subsequently washed with 6 ml of Tris-HCl buffer, 4° C. Bound radioactivity was counted on an LKB Beta-plate Liquid Scintillation Counter and expressed in counts per minute (cpm). To determine inter- and intra-assay variation, standard curves in which $[^{3}H]$-DAGo was incubated in the presence of a range of concentrations of unlabeled DAGO (0.13 14 3900 nM) were included in each plate of each assay (a 96-well format was used). Competitive inhibition assays were performed as above using serial dilutions of the peptide mixtures. $IC_{50}$ values (the concentration necessary to inhibit 50 percent of $[^{3}H]$-DAGO binding) were then calculated. These were found to be consistent in three separate determinations.

EXAMPLE 6

Positional Scanning Assay

Another assay was begun to determine the sequence of an optimal binding dimer ligand for monoclonal antibody 17D09. The same assay procedures were used here as in Example 2, except the dimer oligopeptide mixture sets utilized were different.

Here, six groups of precursor molecules were prepared. Each group had an acetyl group at the N-terminus of each polypeptide chain, and an amide group at the C-terminus of each chain. Each oligopeptide of each group contained a chain of seven residues, with a cysteine at position 4. Each precursor group had a single one of the before-discussed nineteen residues at one position in the chain and had equimolar mixtures of residues at the remaining five chain positions. Each precursor group differed from the other groups by the chain position of the single, predetermined residue and concomitant change of one equimolar mixture position. Thus, group 1 had a single residue at position 1 (N-terminus) a cysteine at position 4 and equimolar mixtures of residues at the remaining positions; group 2 had a single residue at position 2, cysteine at position 4 and equimolar mixtures at the remaining positions; and so on for the remaining groups. Each group therefore also contained nineteen different sub-group mixtures of oligopeptides, one for each of the nineteen different single predetermined residues.

Each sub-group mixture within each group is reacted with itself and the other sub-group members of the group as described in Example 1 to form six libraries of dimeric oligopeptide mixture sets, each library containing 190 different mixture sets. A total of 1140 dimeric mixture sets is thus prepared.

Preparation of the 190 dimeric oligopeptide mixture sets in which position 3 contained the known, predetermined residue and screening of those dimeric sets provided no significant binding inhibition in the assay of Example 2. The reason for this observation is being examined and could be due simply to positional redundancy. Further studies are underway.

The foregoing is intended as illustrative of the present invention but not limiting. Numerous variations and modifications may be effected without departing from the true spirit and scope of the novel concepts of the invention.

---

What is claimed is:

1. A dimeric oligopeptide mixture set comprised of dimer molecules having two bonded portions in which the oligopeptide chains of a first oligopeptide portion are bonded by a disulfide bond to the oligopeptide chains of a second oligopeptide mixture portion, wherein (A) each oligopeptide in said first oligopeptide portion has
    (a) a chain that contains the same number of 3 to about 10 amino acid residues, including an oxidized mercaptan-containing residue that is located at the same position in each oligopeptide chain and forms part of said disulfide bond, said oxidized mercaptan-containing residue being the only mercaptan-containing residue in the chain,
    (b) an amino acid residue sequence, in addition to said oxidized mercaptan-containing residue, that contains one of at least six predetermined amino acid residues at the same, one or more predetermined positions of the oligopeptide chain; and (B) each oligopeptide in said second oligopeptide mixture portion bonded to said first oligopeptide portion has
    (a) a chain that contains the same number of 3 to about 10 amino acid residues, including an oxidized mercaptan-containing residue that is located at the same position in each oligopeptide chain and forms a part of said disulfide bond, said oxidized mercaptan-containing residue being the only mercaptan-containing residue present in the chain, and said second oligopeptide mixture having equimolar amounts of said at least six different amino acid residues at the same one or more other positions of the oligopeptide chain;

said dimeric oligopeptide mixture set being substantially free of oligopeptide molecules having no disulfide bond.

2. The dimeric oligopeptide mixture set according to claim 1 wherein said second oligopeptide mixture portion is the same as said first oligopeptide portion and the molecules of said dimeric oligopeptide mixture set are homodimers.

3. The dimeric oligopeptide mixture set according to claim 1 wherein the chains of said second oligopeptide mixture portion are different from the chains of said first oligopeptide portion, and the molecules of said dimeric oligopeptide mixture set are heterodimers.

4. The dimeric oligopeptide mixture set according to claim 3 wherein each oligopeptide chain of said second oligopeptide mixture portion has an amino acid residue sequence, in addition to said oxidized mercaptan-containing residue, that contains one of at least six predetermined amino acid residues at the same, one or more predetermined position of the oligopeptide chain.

5. The dimeric oligopeptide mixture set according to claim 1 wherein said first oligopeptide portion is a mixture of oligopeptide chains additionally having equimolar amounts of at least six different amino acid residues at the same at least one position of the oligopeptide chains.

6. The dimeric oligopeptide mixture set according to claim 5 that includes homodimer molecules in which oligopeptide chains of said first oligopeptide mixture portion are bonded to each other by a disulfide bond formed from said oxidized mercaptan-containing residues, and homodimer molecules in which oligopeptide chains of said second oligopeptide mixture portion are bonded to each other by a disulfide bond formed from said oxidized mercaptan-containing residues.

7. The dimeric oligopeptide mixture set according to claim 5 wherein the length of the oligopeptides of said first oligopeptide mixture portion is the same as the length of the oligopeptides of said second oligopeptide mixture portion.

8. The dimeric oligopeptide mixture set according to claim 1 wherein the oxidized mercaptan-containing residue in said first oligopeptide portion and in said second oligopeptide mixture portion is positioned at other than the amino-terminus or carboxy-terminus of each oligopeptide chain.

9. The dimeric oligopeptide mixture set according to claim 1 wherein the amino-terminus of each oligopeptide chain is an amino group, a $C_1$–$C_{18}$ straight or branched chain hydrocarbamide, or pyroglutamide group, and the carboxyl-terminus of each oligopeptide chain is a carboxyl or carboxamide group.

10. The dimeric oligopeptide mixture set according to claim 5 wherein at least 10 different amino acid residues are present at each position of equimolarity in both said first and said second oligopeptide mixture portions, and the one predetermined amino acid residue at the same, one or more predetermined positions of the oligopeptide chain is one of the same at least 10 different amino acid residues.

11. A dimeric oligopeptide mixture set comprised of dimer molecules having two bonded portions, said dimer molecules being selected from the group consisting of heterodimers and homodimers, wherein (I) said heterodimer molecules comprise a first oligopeptide mixture portion whose oligopeptide chains are bonded by a disulfide bond to the oligopeptide chains of a second oligopeptide mixture, wherein (A) each oligopeptide in said first oligopeptide mixture has
   (a) a chain that contains the same number of 3 to about 10 amino acid residues, including an oxidized mercaptan-containing residue that is located at the same position in each oligopeptide chain and forms part of said disulfide bond, said oxidized mercaptan-containing residue being the only mercaptan-containing residue present in the chain,
   (b) an amino acid residue sequence, in addition to said oxidized mercaptan-containing residue, that contains one of at least six predetermined amino acid residues at the same one or more, predetermined positions of the oligopeptide chain, and
said first oligopeptide mixture portion having equimolar amounts of said at least six different amino acid residues at the same one or more other position of the oligopeptide chain; and (B) each oligopeptide in said second oligopeptide mixture portion bonded to said first oligopeptide mixture has
   (a) a chain that contains the same number of 3 to about 10 amino acid residues, including an oxidized mercaptan-containing residue that is located at the same position in each oligopeptide chain and forms a part of said disulfide bond, said oxidized mercaptan-containing residue being the only mercaptan-containing residue present in the chain, and
said second oligopeptide mixture portion having equimolar amounts of said at least six different amino acid residues at the same one or more other positions of the oligopeptide chain; and (II) said homodimer molecules comprise oligopeptide chains of said first oligopeptide mixture portion that are bonded to each other by a disulfide bond formed from said oxidized mercaptan-containing residues, and homodimer molecules in which oligopeptide chains of said second oligopeptide mixture portion are bonded to each other by a cystine formed from said oxidized mercaptan-containing residues;

said dimeric oligopeptide mixture set being substantially free of oligopeptide molecules having no disulfide bond.

12. The dimeric oligopeptide mixture set according to claim 11 wherein the length of the oligopeptides of said first oligopeptide mixture portion is the same as the length of the oligopeptides of said second oligopeptide mixture portion.

13. The dimeric oligopeptide mixture set according to claim 11 wherein the oxidized mercaptan-containing residue in said first oligopeptide mixture portion and in said second oligopeptide mixture is positioned at other than the amino-terminus or carboxy-terminus.

14. The dimeric oligopeptide mixture set according to claim 11 wherein the amino-terminus of each oligopeptide chain is an amino group, a $C_1$–$C_{18}$ straight or branched chain hydrocarbamide, or pyroglutamide group, and the carboxyl-terminus of each oligopeptide chain is a carboxyl or carboxamide group.

15. The dimeric oligopeptide mixture set according to claim 11 that is free of heterodimer molecules.

16. The dimeric oligopeptide mixture set according to claim 11 at least 10 different amino acid residues are present at each position of equimolarity in both said first and said second oligopeptide mixture portions, and the one predetermined amino acid residue at the same, one or more predetermined positions of the oligopeptide chain is one of the same at least 10 different amino acid residues.

17. The dimeric oligopeptide mixture set according to claim 11 wherein said mercaptan-containing residue is cysteine.

18. A library of dimeric oligopeptide mixture sets that comprises a plurality of sets of dimeric oligopeptide mixtures, each set of dimeric oligopeptide mixtures comprised of dimer molecules having two bonded portions in which the oligopeptide chains of a first oligopeptide portion are bonded by a disulfide bond to the oligopeptide chains of a second oligopeptide mixture portion, wherein (A) each oligopeptide in said first oligopeptide portion has
   (a) a chain that contains the same number of 3 to about 10 amino acid residues, including an oxidized mercaptan-containing residue that is located at the same position in each oligopeptide chain and forms part of said disulfide bond, said oxidized mercaptan-containing residue being the only mercaptan-containing residue in the chain,
   (b) an amino acid residue sequence, in addition to said oxidized mercaptan-containing residue, that contains one of at least six predetermined amino acid residues at the same, one or more predetermined positions of the oligopeptide chain; and (B) each oligopeptide in said second oligopeptide mixture portion bonded to said first oligopeptide portion has
(a) a chain that contains the same number of 3 to about 10 amino acid residues, including an oxidized mercaptan-containing residue that is located at the same position in each oligopeptide chain and forms a part of said disulfide bond, said oxidized mercaptan-containing residue being the only mercaptan-containing residue present in the chain, and said second oligopeptide mixture portion having equimolar amounts of said at least six different amino acid residues at the same one or more other positions of the oligopeptide chain;

said dimeric oligopeptide mixture set being substantially free of oligopeptide molecules having no disulfide bond;

each set of said library having the same length, position of the oxidized mercaptan-containing residue in each chain, and number of chain positions occupied by equimolar mixtures of the same at least six different amino acid residues, and each set in said library differing from the other sets in:
(a) the position of the one or more predetermined amino acid residues in the oligopeptide chain,
(b) the identity of the one or more predetermined amino acid residues, or
(c) both the position and identity of the one or more predetermined amino acid residues.

19. The library of dimeric oligopeptides according to claim 18 wherein said second oligopeptide mixture portion is the same as said first oligopeptide portion and the molecules of said dimeric oligopeptide mixture set are homodimers.

20. The library of dimeric oligopeptides according to claim 18 wherein the chains of said second oligopeptide mixture portion are different from the chains of said first oligopeptide portion, and the molecules of said dimeric oligopeptide mixture set are heterodimers.

21. The library of dimeric oligopeptides according to claim 20 wherein each oligopeptide chain of said second oligopeptide mixture portion has an amino acid residue sequence, in addition to said oxidized mercaptan-containing residue, that contains one of at least six predetermined amino acid residues at the same, one or more predetermined position of the oligopeptide chain.

22. The library of dimeric oligopeptides according to claim 18 wherein said first oligopeptide portion is a mixture of oligopeptide chains additionally having equimolar amounts of at least six different amino acid residues at the same at least one position of the oligopeptide chains.

23. The library of dimeric oligopeptides according to claim 18 wherein said oxidized mercaptan-containing residue is at other than the carboxy-terminus or amino-terminus of the oligopeptide chains of said first oligopeptide portion and said second oligopeptide portion.

24. A library of dimer oligopeptides that comprises a plurality of sets of dimeric oligopeptide mixtures, each set of dimeric oligopeptide mixtures being comprised of dimer molecules having two bonded portions, said dimer molecules being selected from the group consisting of heterodimers and homodimers, wherein (I) said heterodimer molecules comprise a first oligopeptide mixture portion whose oligopeptide chains are bonded by a disulfide bond to the oligopeptide chains of a second oligopeptide mixture, wherein (A) each oligopeptide in said first oligopeptide mixture has
(a) a chain that contains the same number of 3 to about 10 amino acid residues, including an oxidized mercaptan-containing residue that is located at the same position in each oligopeptide chain and forms part of said disulfide bond, said oxidized mercaptan-containing residue being the only mercaptan-containing residue present in the chain,
(b) an amino acid residue sequence, in addition to said oxidized mercaptan-containing residue, that contains one of at least six predetermined amino acid residues at the same one or more, predetermined positions of the oligopeptide chain, and said first oligopeptide mixture portion having equimolar amounts of said at least six different amino acid residues at the same one or more other position of the oligopeptide chain; and (B) each oligopeptide in said second oligopeptide mixture portion bonded to said first oligopeptide mixture has
(a) a chain that contains the same number of 3 to about 10 amino acid residues, including an oxidized mercaptan-containing residue that is located at the same position in each oligopeptide chain and forms a part of said disulfide bond, said oxidized mercaptan-containing residue being the only mercaptan-containing residue present in the chain, and said second oligopeptide mixture portion having equimolar amounts of said at least six different amino acid residues at the same one or more other positions of the oligopeptide chain; and (II) said homodimer molecules comprise oligopeptide chains of said first oligopeptide mixture portion that are bonded to each other by a disulfide bond formed from said oxidized mercaptan-containing residues, and homodimer molecules in which oligopeptide chains of said second oligopeptide mixture portion are bonded to each other by a disulfide bond formed from said oxidized mercaptan-containing residues;

said dimeric oligopeptide mixture set being substantially free of oligopeptide molecules having no disulfide bond;

each set of said library having the same length, position of the oxidized mercaptan-containing residue in each chain, and number of chain positions occupied by equimolar mixtures of the same at least six different amino acid residues, and each set in said library differing from the other sets in:
(a) the position of the one or more predetermined amino acid residues in the oligopeptide chain,
(b) the identity of the one or more predetermined amino acid residues, or
(c) both the position and identity of the one or more predetermined amino acid residues.

25. The library of dimeric oligopeptides according to claim 24 wherein the length of the oligopeptides of said first oligopeptide mixture portion is the same as the length of the oligopeptides of said second oligopeptide mixture portion.

26. The library of dimeric oligopeptides according to claim 24 wherein said oxidized mercaptan-containing residue in said first oligopeptide mixture portion and in said second oligopeptide mixture portion is positioned at other than the amino-terminus or carboxy-terminus.

27. The library of dimeric oligopeptides according to claim 23 that is free of heterodimer molecules.

28. The library of dimeric oligopeptides according to claim 24 wherein at least 10 different amino acid residues are present at each position of equimolarity in both said first and said second oligopeptide mixture portion, and the one predetermined amino acid residue at the same, one or more predetermined positions of the oligopeptide chain is one of the same at least 10 different amino acid residues.

29. The library of dimeric oligopeptides according to claim 24 wherein said mercaptan-containing residue is cysteine.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear

```
        (ii) MOLECULE TYPE: peptide (ix) FEATURE:
             (A) NAME/KEY: Peptide
             (B) LOCATION: 1..4
             (D) OTHER INFORMATION: /label= Xaa
                 /note= "Xaa in this peptide represents a mixture
                 of at least six amino acid residues other than
                 a mercaptan-containing residue."

(xi) SEQUENCE DESCRIPTION: SEQ ID NO:1:

Xaa Cys Xaa Xaa
1

(2) INFORMATION FOR SEQ ID NO:2:

(i) SEQUENCE CHARACTERISTICS:
             (A) LENGTH: 13 amino acids
             (B) TYPE: amino acid
             (D) TOPOLOGY: linear (ii) MOLECULE TYPE: peptide (xi) SEQUENCE DESCRIPTION: SEQ ID NO:2:

Tyr Pro Tyr Asp Val Pro Asp Tyr Ala Ser Leu Arg Ser
1               5                   10

(2) INFORMATION FOR SEQ ID NO:3:

(i) SEQUENCE CHARACTERISTICS:
             (A) LENGTH: 4 amino acids
             (B) TYPE: amino acid
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /label= Xaa
                 /note= "Xaa is acetyl methionine sulfoxide."

(ix) FEATURE:
             (A) NAME/KEY: Modified-site
             (B) LOCATION: 4
             (D) OTHER INFORMATION: /label= Xaa
                 /note= "Xaa is Arg-NH2."

(xi) SEQUENCE DESCRIPTION: SEQ ID NO:3:

Xaa Cys Trp Xaa
1

(2) INFORMATION FOR SEQ ID NO:4:

(i) SEQUENCE CHARACTERISTICS:
             (A) LENGTH: 4 amino acids
             (B) TYPE: amino acid
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /label= Xaa
                 /note= "Xaa is acetly methionine sulfoxide."

(ix) FEATURE:
             (A) NAME/KEY: Disulfide-bond
             (B) LOCATION: 2
             (D) OTHER INFORMATION: /note= "SEQ ID NO:4 represents a
                 homodimer of the listed sequence, joined by a
                 disulfide bond at the Cys residues."
```

```
        (ix) FEATURE:
             (A) NAME/KEY: Modified-site
             (B) LOCATION: 4
             (D) OTHER INFORMATION: /label= Xaa
                  /note= "Xaa is Arg-NH2."

(xi) SEQUENCE DESCRIPTION: SEQ ID NO:4:

Xaa Cys Trp Xaa
1

(2) INFORMATION FOR SEQ ID NO:5:

(i) SEQUENCE CHARACTERISTICS:
             (A) LENGTH: 5 amino acids
             (B) TYPE: amino acid
             (D) TOPOLOGY: linear (ii) MOLECULE TYPE: peptide (xi) SEQUENCE DESCRIPTION: SEQ ID NO:5:

Tyr Gly Gly Phe Met
1               5

(2) INFORMATION FOR SEQ ID NO:6:

(i) SEQUENCE CHARACTERISTICS:
             (A) LENGTH: 5 amino acids
             (B) TYPE: amino acid
             (D) TOPOLOGY: linear (ii) MOLECULE TYPE: peptide (xi) SEQUENCE DESCRIPTION: SEQ ID NO:6:

Tyr Gly Gly Phe Leu
1               5
```